(12) United States Patent
Woodard, Jr. et al.

(10) Patent No.: US 9,168,037 B2
(45) Date of Patent: Oct. 27, 2015

(54) LAPAROSCOPIC SUTURE DEVICE WITH ASYNCHRONOUS IN-LINE NEEDLE MOVEMENT

(75) Inventors: James A. Woodard, Jr., Mason, OH (US); Frederick E. Shelton, IV, Hillsboro, OH (US); Jason R. Lesko, Harrison, OH (US); Chester O. Baxter, III, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1155 days.

(21) Appl. No.: 13/156,420

(22) Filed: Jun. 9, 2011

(65) Prior Publication Data
US 2011/0313433 A1 Dec. 22, 2011

Related U.S. Application Data

(60) Provisional application No. 61/355,832, filed on Jun. 17, 2010.

(51) Int. Cl.
*A61B 17/062* (2006.01)
*A61B 17/04* (2006.01)
*A61B 17/29* (2006.01)

(52) U.S. Cl.
CPC ........... *A61B 17/062* (2013.01); *A61B 17/0469* (2013.01); *A61B 17/0482* (2013.01); *A61B 2017/2936* (2013.01)

(58) Field of Classification Search
CPC ............. A61B 17/0469; A61B 17/062; A61B 17/0482; A61B 2017/2936; A61B 2017/0609
USPC .............. 606/144–146, 148; 289/17; 112/169
See application file for complete search history.

(56) References Cited

U.S. PATENT DOCUMENTS

| | | | | |
|---|---|---|---|---|
| 5,908,428 | A | * | 6/1999 | Scirica et al. ................ 606/139 |
| 5,993,466 | A | * | 11/1999 | Yoon ............................ 606/147 |
| 6,071,289 | A | | 6/2000 | Stefanchik et al. |
| 6,224,614 | B1 | * | 5/2001 | Yoon ............................ 606/147 |
| 7,628,796 | B2 | | 12/2009 | Shelton, IV et al. |
| 8,137,339 | B2 | | 3/2012 | Jinno et al. |
| 2012/0165837 | A1 | * | 6/2012 | Belman et al. ................ 606/144 |

* cited by examiner

*Primary Examiner* — Julian W Woo
*Assistant Examiner* — Shaun L David
(74) *Attorney, Agent, or Firm* — Frost Brown Todd LLC

(57) ABSTRACT

An apparatus comprises a shaft, a needle throwing arm, and a needle receiving arm. The arms are movable asynchronously along planes that are substantially parallel to a longitudinal axis defined by the shaft. The arms selectively engage a surgical needle, such that the throwing arm may pass the surgical needle through tissue for receipt by the receiving arm, and the receiving arm may then pass the surgical needle back to the throwing arm for additional stitching. The arms may pivot about a common pivot. Such versions may include a single actuator for both arms or separate actuators for the arms. The arms may also pivot about their own respective axles, which may facilitate a forward reset motion for a needle, allowing the needle to continue travelling along a circular path in a single direction to create several stitches. The apparatus may also convert reciprocating movement of actuators into rotational motion.

6 Claims, 34 Drawing Sheets

LAPAROSCOPIC SUTURE DEVICE WITH ASYNCHRONOUS IN-LINE NEEDLE MOVEMENT

PRIORITY

This application claims priority to U.S. Provisional Application Ser. No. 61/355,832, filed Jun. 17, 2010, entitled "Laparoscopic Suture Device," the disclosure of which is incorporated by reference herein.

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparascopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio. Additional suturing instruments are disclosed in U.S. Pat. No. 7,628,796, entitled "Surgical Suturing Apparatus with Anti-Backup System," issued Dec. 8, 2009, the disclosure of which is incorporated by reference herein; and U.S. Pat. No. 6,071,289, entitled "Surgical Device for Suturing Tissue," issued Jun. 6, 2000, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. OVERVIEW

Figure 1:
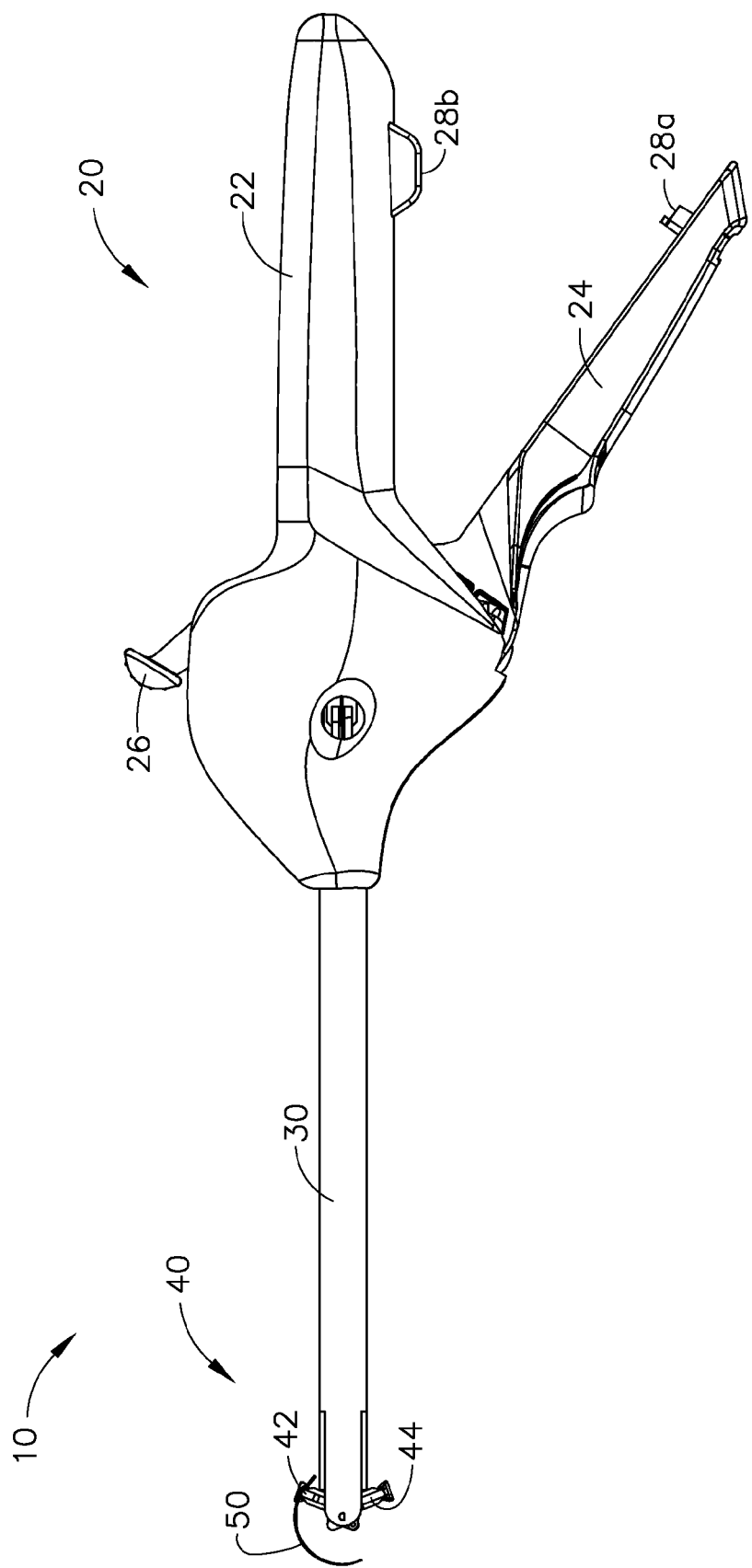
FIG. 1 depicts a side elevational view of an exemplary laparoscopic suturing device, in a first operational configuration.
Figure 2:
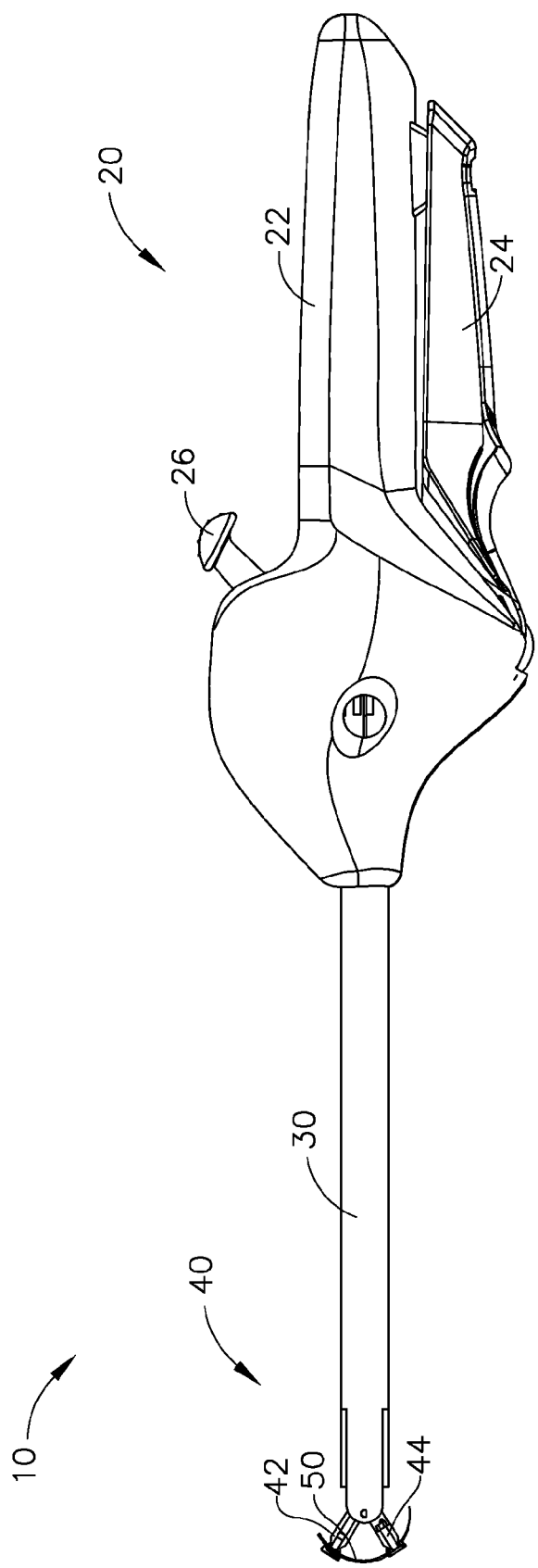
FIG. 2 depicts a side elevational view of the suturing device of FIG. 1, in a second operational configuration.
Figure 3:
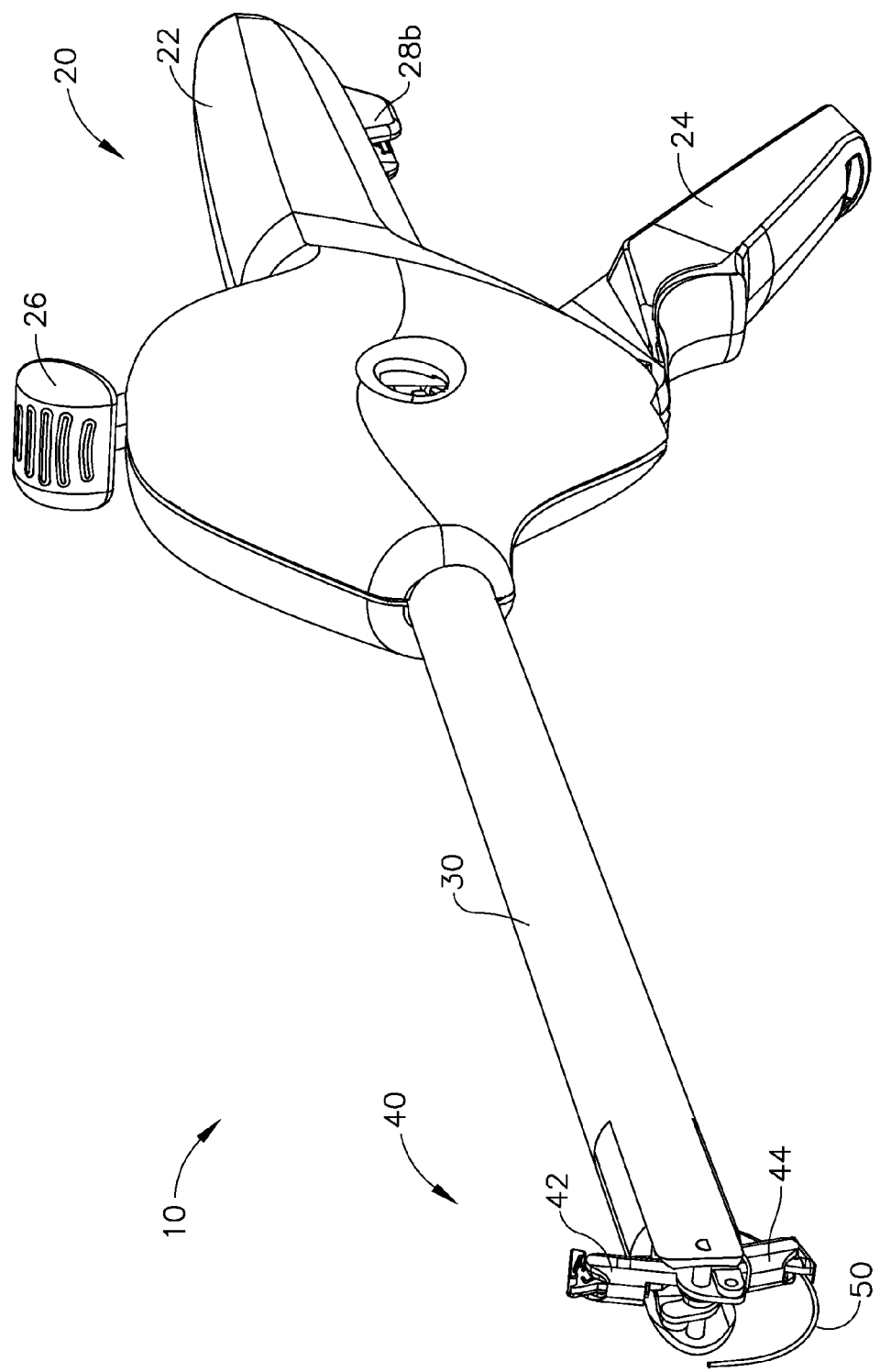
FIG. 3 depicts a perspective view of the suturing device of FIG. 1, in a third operational configuration.

FIGS. 1-3 show an exemplary laparoscopic suturing instrument (10). Instrument (10) of this example includes a handle portion (20), a shaft (30) extending distally from handle portion (20), and an end effector (40) at the distal end of shaft (30). Handle portion (20) includes a fixed grip (22), a pivoting grip (24), and a button (26). Pivoting grip (24) and button (26) are each resiliently biased to the positions shown in FIG. 1, such as by one or more springs, etc. Pivoting grip (24) and button (26) may each be pushed toward fixed grip (22) to actuate features of end effector (40) as will be described in greater detail below. Various other suitable components, features, and configurations for handle portion (20) will be apparent to those of ordinary skill in the art in view of the teachings herein.

Shaft (30) of the present example has an outer diameter sized to permit shaft (30) to be inserted through a conventional trocar (not shown). Shaft (30) also has a length sized to permit end effector (40) to be positioned at a surgical site within a patient while also allowing handle portion (20) to be manipulated by a user (e.g., a surgeon) from a location outside the patient when shaft (30) is disposed in a trocar. In some versions, shaft (30) includes one or more articulating features, allowing end effector (40) to be articulated to various angles and positions relative to the longitudinal axis defined by shaft (30). Merely illustrative examples of such articulation are taught in U.S. Provisional Application Ser. No. 61/355,832, the disclosure of which is incorporated by reference herein. Various other suitable ways in which articulation may be provided will be apparent to those of ordinary skill in the art in view of the teachings herein. In addition or in the alternative, shaft (30) may be rotatable about the longitudinal axis, relative to handle portion (20), to selectively position end effector (40) at various angular orientations about the longitudinal axis.

End effector (40) of the present example includes a first arm (42) and a second arm (44). Arms (42, 44) are configured to alternatingly throw and catch a curved suturing needle (50) along a path that is substantially parallel to the longitudinal axis defined by shaft (30). Alternatively, arms (42, 44) may be configured to alternatingly throw and catch needle (50) along a path that is substantially perpendicular to the longitudinal axis defined by shaft (30); or along some other path. In addition, arms (42, 44) of the present example pass needle (50) back and forth from arm (42) to arm (44) and from arm (44) to arm (42) in an oscillating motion (i.e., back and forth in opposite directions), such that needle (50) does not traverse a circular path as needle (50) is being passed between arms (42, 44). Such action of needle (50) may be referred to as a "reverse reset." In some other versions, such as those described below in section III, needle (50) may be passed between arms along a circular path in a single direction. Such action of needle (50) may be referred to as a "forward reset." When separated as shown in FIG. 1, arms (42, 44) may together define an angle of approximately 90°. Alternatively, arms (42, 44) may together define an angle of up to approximately 270°, or even greater than approximately 270°. Arms (42, 44) are operatively coupled with pivoting grip (24) and button (26). In particular, pivoting grip (24) is operable to move arms (42, 44) toward each other when pivoting grip (24) is squeezed toward fixed grip (22), as shown in FIG. 2. In some versions, handle portion (20) includes a rack and pinion configuration, with a translating member moving within shaft (30), and a camming feature at end effector (40) to provide such movement of arms (42, 44) in response to actuation of pivoting grip (24). Merely illustrative examples of such features are taught in U.S. Provisional Application Ser. No. 61/355,832, the disclosure of which is incorporated by reference herein. Various other suitable ways in which movement of arms (42, 44) may be provided in response to actuation of pivoting grip (24) will be apparent to those of ordinary skill in the art in view of the teachings herein. As noted above, pivoting grip (24) is resiliently biased to the position shown in FIG. 1. Pivoting grip (24) and fixed grip (22) include complementary latching features (28a, 28b) that are operable to selectively lock pivoting grip (24) to the actuated position shown in FIG. 2, resisting that resilient bias. As with other features described herein, latching features (28a, 28b) are merely optional and may be modified, substituted, supplemented, or omitted as desired.

In the present example, as arms (42, 44) throw and catch needle (50) to each other, arms (42, 44) move toward and away from each other (and toward and away from the longitudinal axis defined by shaft (30)) in a synchronous manner. For instance, the transition from FIG. 1 to FIG. 2 shows arms (42, 44) moving toward each other, with arm (42) throwing needle (50) to arm (44). The transition from FIG. 2 to FIG. 3 shows arms (42, 44) moving away from each other, with arm (44) having caught needle (50). In the present example, button (26) is used to actuate features in arms (42, 44) to selectively grip and release needle (50). For instance, when arms (42, 44) are approximated as shown in FIG. 2, with arm (42) throwing needle (50) to arm (44), button (26) may be actuated to simultaneously release needle (50) from arm (42) and grip needle (50) with arm (44). Examples of various suitable components, features, and configurations that may be used to provide such selective gripping of needle (50) by arms (42, 44) are taught in U.S. Provisional Application Ser. No. 61/355,832, the disclosure of which is incorporated by reference herein. Still other suitable components, features, and configurations that may be used to provide selective gripping of needle (50) by arms (42, 44) will be apparent to those of ordinary skill in the art in view of the teachings herein. It should also be understood that needle (50) may also include features to facilitate selective gripping, including but not limited to one or more notches, etc.

In some other versions, arms (42, 44) move toward and away from each other (and toward and away from the longitudinal axis defined by shaft (30)) in an asynchronous manner. For instance, in some versions of asynchronous movement, arm (42) may first move toward the longitudinal axis while arm (44) stays stationary; then arm (44) moves toward the longitudinal axis while arm (42) stays stationary, with arm (44) catching needle (50); then arm (42) moves away from the longitudinal axis while arm (44) stays stationary; then arm (44) moves away from the longitudinal axis while arm (42) stays stationary. As another merely illustrative example of asynchronous movement, arm (42) may first move toward the longitudinal axis while arm (44) stays stationary; then arm (44) moves toward the longitudinal axis while arm (42) stays stationary, with arm (44) catching needle (50); then arms (42, 44) move simultaneously away from the longitudinal axis. Various examples of components and configurations that may be used to provide asynchronous movement will be described in greater detail below, while other examples will be apparent to those of ordinary skill in the art in view of the teachings herein. Regardless of whether arms (42, 44) move synchronously or asynchronously, arms (42, 44) may be configured to grip and/or compress tissue that is positioned between arms (42, 44) when arms are in approximated positions, which may facilitate passage of needle (50) through the tissue.

In some versions, needle (50) has a sharp tip at one end of needle (50) and a suture (not shown) secured to the opposite end of needle (50). In a merely illustrative example of how instrument (10) may be used with such a needle (50), a user may actuate pivoting grip (24) to throw needle (50) from arm (42) to arm (44), passing needle (50) through tissue. The user may actuate button (26) to release needle (50) from arm (42) and grip needle (50) with arm (44). After releasing pivoting grip (24) to move arms (42, 44) away from the longitudinal axis, the user may then pull instrument (10) away from the surgical site to tighten the suture. Next, with arms (42, 44) positioned away from the surgical site, the user may again actuate pivoting grip (24) to pass needle (50) back to arm (42). Arms (42, 44) may then be positioned back at the surgical site, and the above process may be repeated until the desired number of stitches have been placed at the surgical site. The free end of the suture may then be knotted, clipped, or otherwise secured. In this example, arm (42) serves a dedicated role as the throwing arm each time needle (50) passes through tissue; while arm (44) serves a dedicated role as the catching arm each time needle (50) passes through tissue. In some such versions, the rotational position of shaft (30) may be substantially fixed relative to the surgical site, such that shaft (30) is simply moved along the region to be stitched. The suture may ultimately define a generally helical path in some such versions. In some other variations, shaft (30) is rotated 180° about its longitudinal axis before each time arm (42) drives needle (50) through tissue, such that the suture defines a path resembling a square wave. It should also be understood that, in some versions where the suture is secured to one end of needle (50) instead of being secured to the middle of needle (50), arms (42, 44) may alternate roles as throwing arm and catching arm. Other suitable ways in which instrument (10) may be used with such a needle (50) will be apparent to those of ordinary skill in the art in view of the teachings herein.

In some other versions, both ends of needle (50) include sharp tips and a suture is secured to the middle region of needle (50), between the sharp tips. In a merely illustrative example of how instrument (10) may be used with such a needle (50), a user may actuate pivoting grip (24) to throw needle (50) from arm (42) to arm (44), passing needle (50) through tissue. The user may actuate button (26) to release needle (50) from arm (42) and grip needle (50) with arm (44). After releasing pivoting grip (24) to move arms (42, 44) away from the longitudinal axis, the user may then pull instrument (10) away from the surgical site to tighten the suture. Next, the user may position arms (42, 44) back at the surgical site, and the user may actuate pivoting grip (24) to throw needle (50) from arm (44) back to arm (42), passing needle (50) through tissue. This process may be repeated until the desired number of stitches have been placed at the surgical site. The free end of the suture may then be knotted, clipped, or otherwise secured. In this example, arms (42, 44) alternate between roles as throwing arm and catching arm each time needle (50) passes through tissue. In some such versions, the rotational position of shaft (30) may be substantially fixed relative to the surgical site, such that shaft (30) is simply moved along the region to be stitched. The suture may ultimately define a path resembling a square wave. In some other variations, shaft (30) is rotated 180° about its longitudinal axis before each time arm (42) drives needle (50) through tissue, such that the suture defines a generally helical path. Other suitable ways in which instrument (10) may be used with such a needle (50) will be apparent to those of ordinary skill in the art in view of the teachings herein.

II. EXEMPLARY SUTURE DEVICE WITH SINGLE FIXED AXLE DRIVE ASSEMBLY

A. Exemplary Drive Assembly with Single Fixed Axle and Single Actuator

FIGS. 4-11 depict an exemplary end effector (100) that may be incorporated into instrument (10) as an alternative to end effector (40) described above. It should also be understood that end effector (100) may be incorporated into various other instruments, such that end effector (100) is not limited to instrument (10). End effector (100) of this example is disposed at the distal end of a shaft (130) and includes a pair of arms (142, 144) that selectively throw and catch a needle (150). In particular, arms (142, 144) pivot about a pin (110) in an asynchronous fashion. In some settings, asynchronous movement of arms (142, 144) will provide a surgeon with greater visibility, more flexibility, and/or better maneuverability while suturing. In addition or in the alternative, asynchronous movement of arms (142, 144) may facilitate use of arms (142, 144) to provide traction or apply an opposing force to tissue prior to entry by a needle (150). For instance, the arm (142, 144) that is serving the role of catching arm may move to engage tissue to provide such fraction and opposition before the other arm (144, 142) moves to throw needle (150) through the tissue. Of course, asynchronous movement of arms (142, 144) may provide other results, in addition to or as an alternative to the results noted above.

Pin (110) is secured to a clevis feature (132) of shaft (130), such that the longitudinal position of pin (110) is fixed relative to shaft (130). A block (160) is slidably disposed in shaft (130), and is pivotally coupled with arms (142, 144) by respective links (172, 174). In particular, link (172) is pivotally coupled with a proximal end (146) of arm (142) and is also pivotally coupled with block (160). Link (174) is pivotally coupled with a proximal end (148) of arm (144) and is also pivotally coupled with block (160). Block (160) includes an elongate slot (162) associated with link (172). In particular, link (172) includes a transverse pin (176) that is slidably disposed in slot (162). This relationship between link (172) and block (160) allows block (160) move relative to link (172) during part of the longitudinal range of motion of block (160); while also allowing block (160) to move link (172) during other parts of the longitudinal range of motion of block (160). In other words, slot (162) provides some degree of lost motion as will be described in greater detail below. Block (160) is further coupled with a linear actuator (not shown) disposed along the length of shaft. The linear actuator is selectively activated by pivoting grip (24).

Needle (150) of this example includes a sharp tip (152) at one end and a suture (154) secured to the other end. Alternatively, both ends of needle (150) may include sharp tips, with suture (154) being secured in a middle region of needle (150) between the sharp tips. While needle (150) is curved in this example, some other versions may include use of a straight needle, an angled needle, or any other suitable type of needle.

Figure 4:
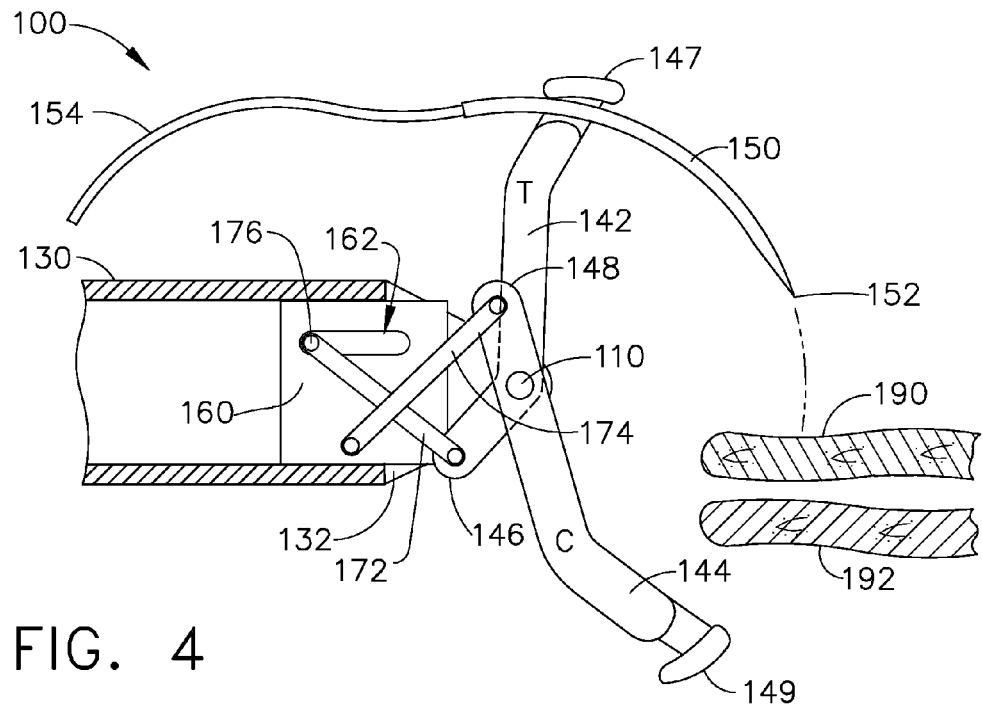
FIG. 4 depicts a partial, cross-sectional side view of an exemplary alternative end effector for a laparoscopic suturing device, in a first operational configuration.

In an exemplary method of operation, end effector (100) is positioned near two layers (190, 192) of tissue, as shown in FIG. 4. Then, pivoting grip (24) is actuated to move block (160) proximally to the position shown in FIG. 5. This proximal movement of block (160) causes link (174) to pull proximal end (148) of arm (144), which in turn pivots the distal end (149) of arm (144) into engagement with lower layer (192) of tissue. Transverse pin (176) slides along the length of slot (162) in block (160) during this stage, such that block (160) does not move link (172). Arm (142) thus remains substantially stationary during this stage. With arm (144) engaging lower layer (192) of tissue, pivoting grip (24) is actuated further to continue moving block (160) proximally to the position shown in FIG. 6. This further proximal movement of block (160) causes link (174) to continue pulling on proximal end (148) of arm (144), which in turn continues to pivot arm (144) into further engagement with lower layer (192) of tissue. In addition, this further proximal movement of block (160) causes link (172) to pull proximal end (146) of arm (142), which in turn pivots the distal end (147) of arm (142) toward upper layer (190) of tissue, thereby driving needle (150) through both layers (190, 192) of tissue. In some other versions, end effector (100) is configured such that arm (144) does not continue pivoting in the transition from the configuration shown in FIG. 5 to the configuration shown in FIG. 6. For instance, block (160) may include an additional slot that provides lost motion for link (174) as block (160) moves from the position shown in FIG. 5 to the position shown in FIG. 6.

Figure 6:
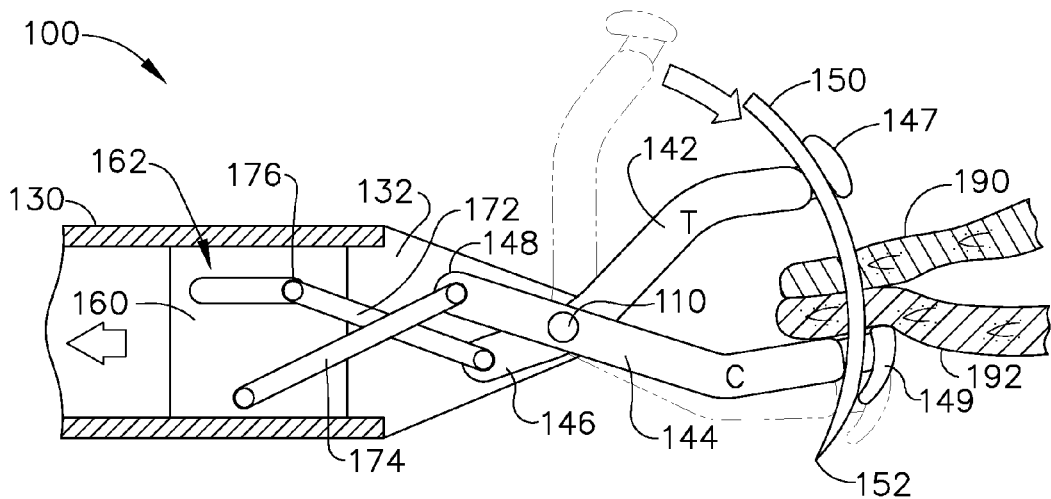
FIG. 6 depicts a partial, cross-sectional side view of the end effector of FIG. 4, in a third operational configuration.

With arms (142, 144) in the positions shown in FIG. 6, the user may then actuate button (26) or some other feature to release needle (150) from arm (142) and grip needle (150) with arm (144). Examples of various suitable components, features, and configurations that may be used to provide such selective gripping of needle (150) by arms (142, 144) are taught in U.S. Provisional Application Ser. No. 61/355,832, the disclosure of which is incorporated by reference herein. Still other suitable components, features, and configurations that may be used to provide selective gripping of needle (150) by arms (142, 144) will be apparent to those of ordinary skill in the art in view of the teachings herein. It should also be understood that needle (150) may also include features to facilitate selective gripping, including but not limited to one or more notches, etc.

Figure 7:
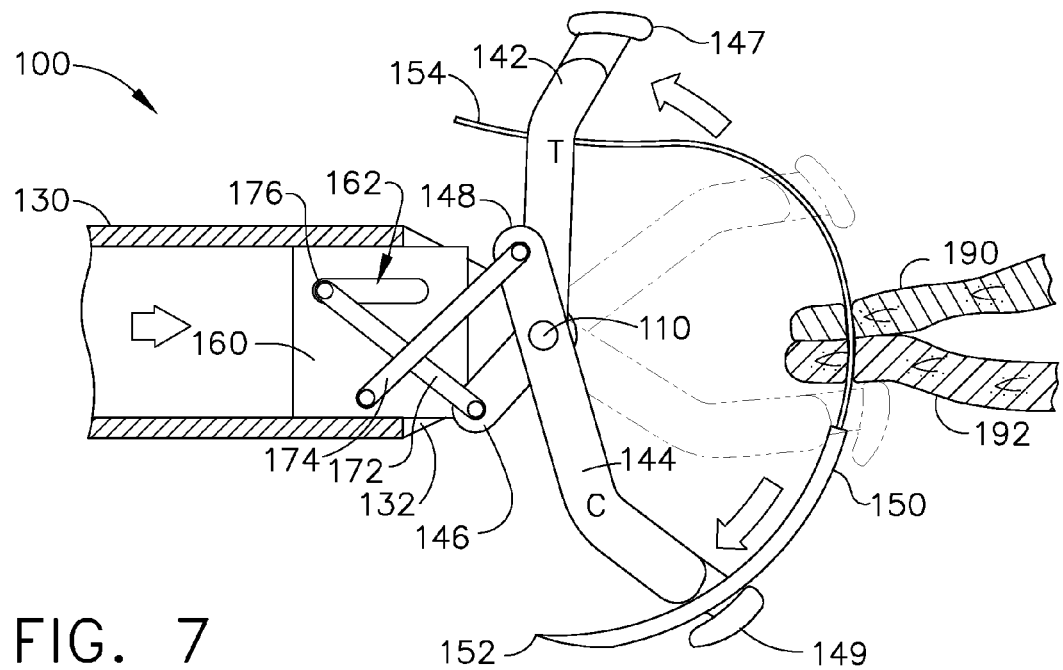
FIG. 7 depicts a partial, cross-sectional side view of the end effector of FIG. 4, in a fourth operational configuration.
Figure 8:
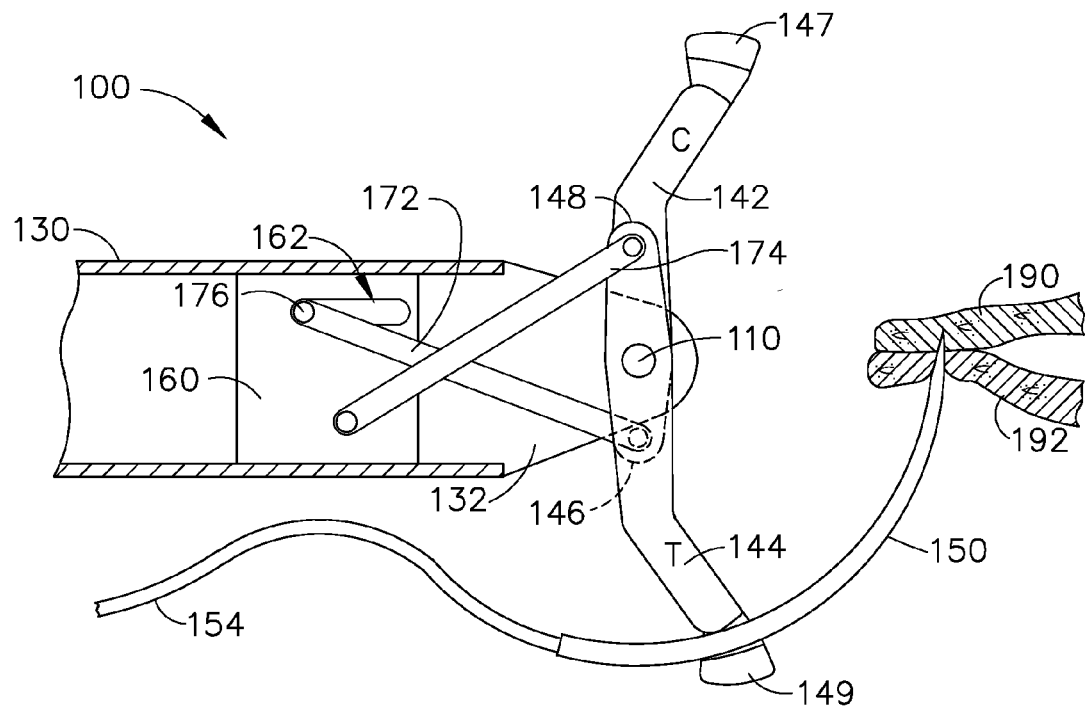
FIG. 8 depicts a partial, cross-sectional side view of the end effector of FIG. 4, in a fifth operational configuration.
Figure 9:
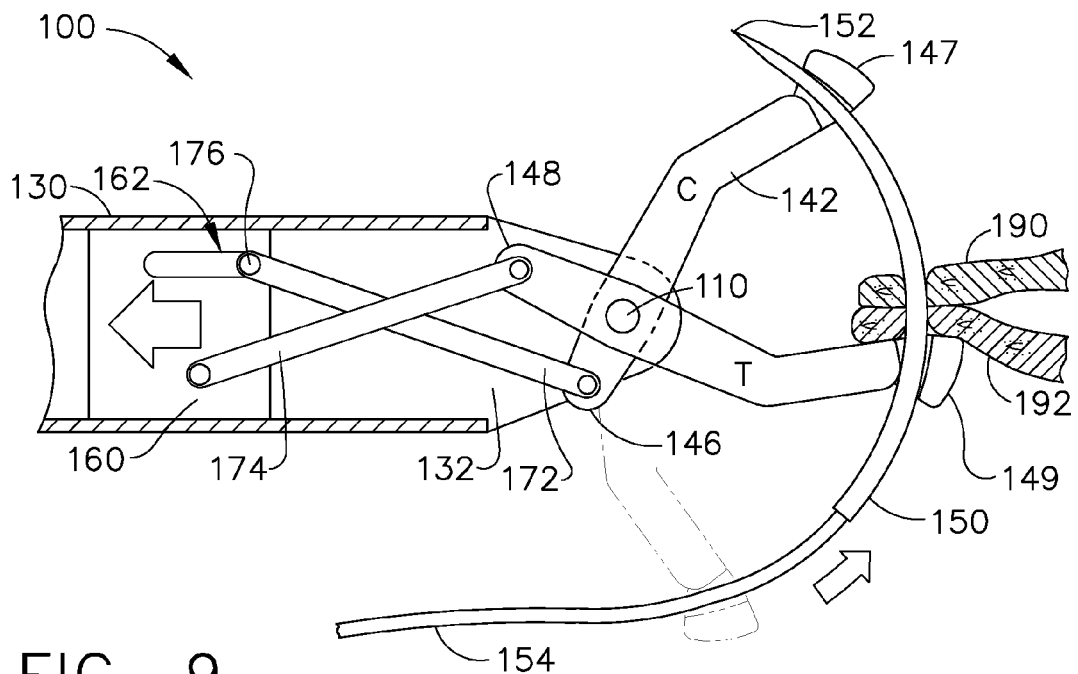
FIG. 9 depicts a partial, cross-sectional side view of the end effector of FIG. 4, in a sixth operational configuration.
Figure 10:
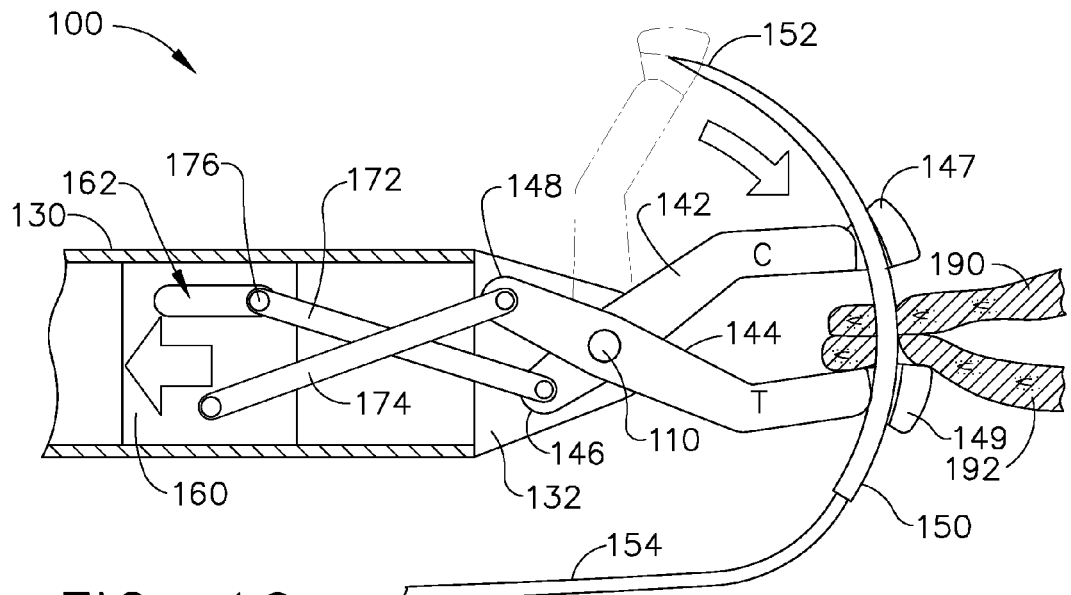
FIG. 10 depicts a partial, cross-sectional side view of the end effector of FIG. 4, in a seventh operational configuration.

With needle (150) having been thrown by arm (142) through both layers (190, 192) of tissue, and with needle (150) having been caught by arm (144), the user may then release pivoting grip (24). A resilient bias may then advance block (160) distally, thereby pivoting arms (142, 144) back to their previous positions, as shown in FIG. 7. This additional movement of arm (144) away from the layers (190, 192) of tissue pulls needle (150) and suture (154) through both layers (190, 192) of tissue. The user may then pull end effector (100) away from layers (190, 192), to pull an additional length of suture (154) through layers (190, 192) and/or to tighten suture (154), if desired. Next, with arms (142, 144) positioned away from the surgical site, the user may again actuate pivoting grip (24) to pass needle (150) back to arm (142) in a "reverse reset" action as referred to above. Arms (142, 144) may then be positioned back at the surgical site, and the above process may be repeated until the desired number of stitches have been placed at the surgical site. The free end of the suture may then be knotted, clipped, or otherwise secured. In this example, arm (142) serves a dedicated role as the throwing arm each time needle (150) passes through layers (190, 192) of tissue; while arm (144) serves a dedicated role as the catching arm each time needle (150) passes through layers (190, 192) of tissue. In some such versions, shaft (130) is rotated 180° about its longitudinal axis before each time arm (142) drives needle (150) through tissue. It should also be understood that, in some versions where suture (154) is secured to one end of needle (150) as well as some versions where suture (154) is secured to the middle of needle (150), arms (142, 144) may alternate roles as throwing arm and catching arm. Other suitable ways in which end effector (100)

may be used with such needles (150) will be apparent to those of ordinary skill in the art in view of the teachings herein.

Figure 5:
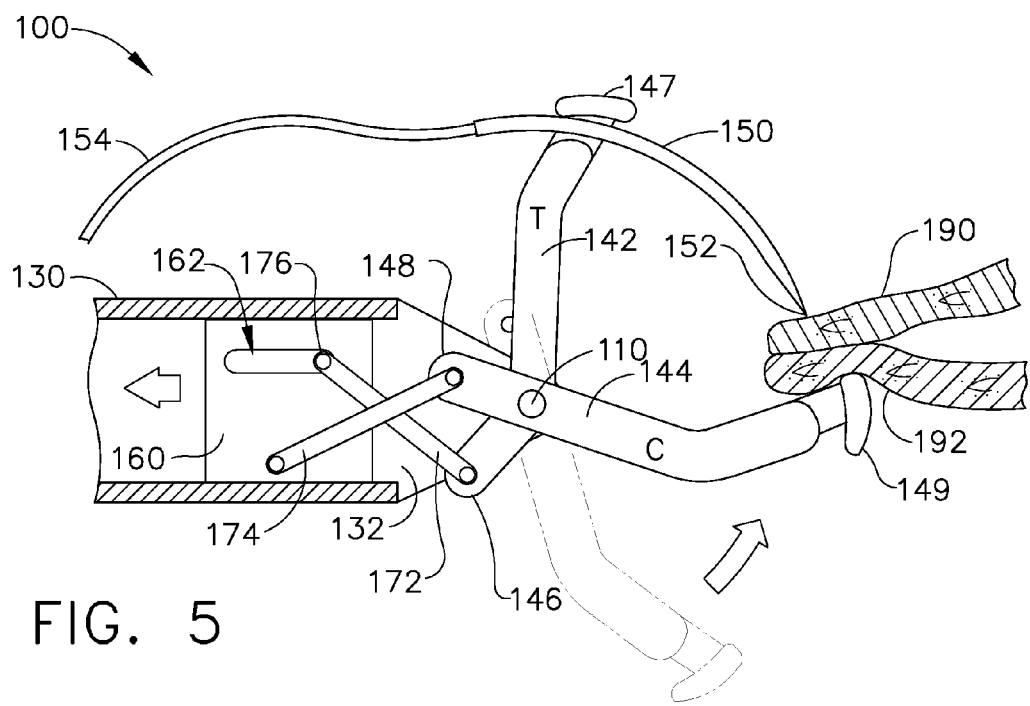
FIG. 5 depicts a partial, cross-sectional side view of the end effector of FIG. 4, in a second operational configuration.

In the present example, pivoting grip (24) actuates arms (142, 144) through the full range of motion depicted in the transition from FIGS. 4-6 with just a single act of squeezing pivoting grip (24) toward fixed grip (22). In some such versions, handle portion (20) may provide audible feedback and/or tactile feedback to the user to indicate that arms (142, 144) have reached the stage shown in FIG. 5 and/or the stage shown in FIG. 6. In some other versions, pivoting grip (24) must be fully actuated once to transition arms (142, 144) from the configuration shown in FIG. 4 to the configuration shown in FIG. 5, then be released, then be fully actuated again to transition arms (142, 144) from the configuration shown in FIG. 5 to the configuration shown in FIG. 6. Various suitable components, features, and configurations that may be used to provide such multi-stroke actuation will be apparent to those of ordinary skill in the art in view of the teachings herein. Similarly, various other suitable ways in which arms (142, 144) may be actuated will be apparent to those of ordinary skill in the art in view of the teachings herein. It should also be understood that block (160) need not necessarily be resiliently biased to a distal position. For instance, block (160) may require some feature of handle portion (20) to be pushed, rotated, and/or otherwise manipulated in order to drive block (160) distally.

Figure 11:
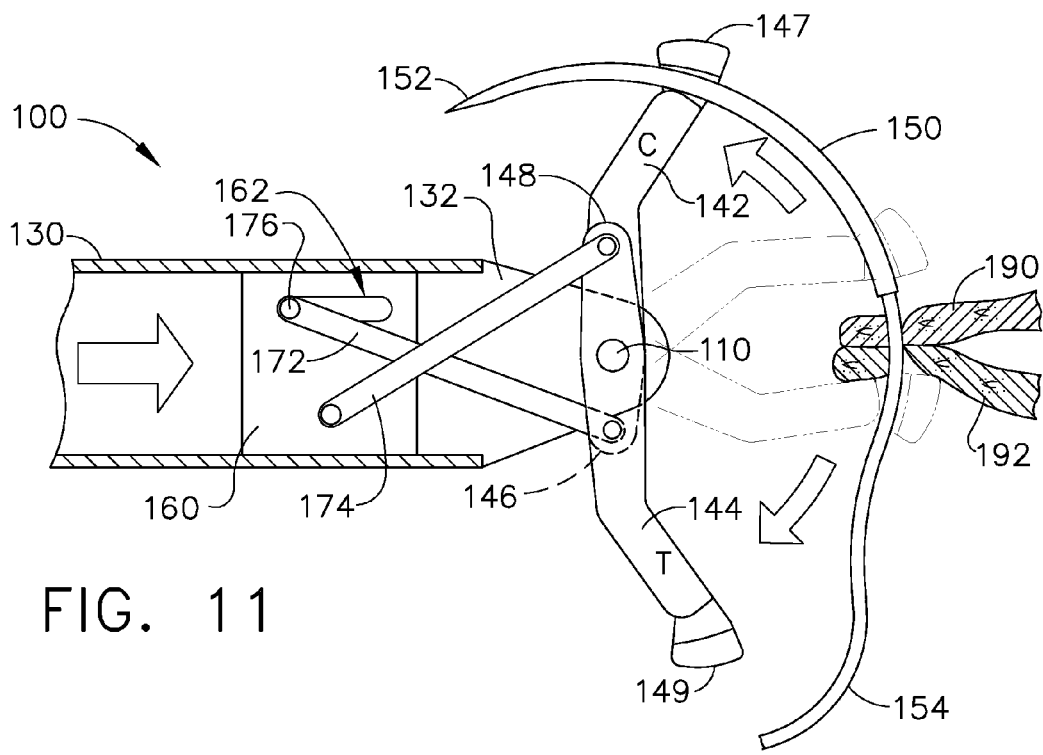
FIG. 11 depicts a partial, cross-sectional side view of the end effector of FIG. 4, in a eighth operational configuration.

FIGS. 8-11 depict exemplary stages of use where the roles of arms (142) are reversed (144). In particular, while FIGS. 4-7 show arm (142) serving the role as a throwing arm and arm (144) serving the role as a catching arm; FIGS. 8-11 show arm (144) serving the role as a throwing arm and arm (142) serving the role as a catching arm. Thus, as pivoting grip (24) is actuated to move block (160) proximally to the position shown in FIG. 9, this proximal movement of block (160) causes link (174) to pull proximal end (148) of arm (144), which in turn pivots the distal end (149) of arm (144) to drive needle (150) through (190, 192) layers of tissue. Again, transverse pin (176) slides along the length of slot (162) in block (160) during this stage, such that block (160) does not move link (172). Arm (142) thus remains substantially stationary during this stage. With needle (150) disposed through layers (190, 192) of tissue, pivoting grip (24) is actuated further to continue moving block (160) proximally to the position shown in FIG. 10. This further proximal movement of block (160) causes link (174) to continue pulling on proximal end (148) of arm (144), which in turn continues to pivot arm (144) into further engagement with lower layer (192) of tissue. In addition, this further proximal movement of block (160) causes link (172) to pull proximal end (146) of arm (142), which in turn pivots the distal end (147) of arm (142) toward upper layer (190) of tissue. With arms (142, 144) in the positions shown in FIG. 10, the user may then actuate button (26) or some other feature to release needle (150) from arm (144) and grip needle (150) with arm (142). With needle (150) having been thrown by arm (144) through both layers of tissue (190, 192), and with needle (150) having been caught by arm (142), the user may then release pivoting grip (24). A resilient bias may then advance block (160) distally, thereby pivoting arms (142, 144) back to their previous positions, as shown in FIG. 11. This additional movement of arm (142) away from the layers of tissue (190, 192) pulls needle (150) and suture (154) through both layers (190, 192) of tissue.

B. Exemplary Drive Assembly with Single Fixed Axle and Dual Actuators

FIGS. 12-15 depict another exemplary end effector (200) that may be incorporated into instrument (10) as an alternative to end effector (40) described above. It should also be understood that end effector (200) may be incorporated into various other instruments, such that end effector (200) is not limited to instrument (10). End effector (200) of this example is disposed at the distal end of a shaft (230) and includes a pair of arms (242, 244) that selectively throw and catch a needle (250). In particular, arms (242, 244) pivot about a pin (210) in an asynchronous fashion. Pin (210) is secured to a clevis feature (232) of shaft (230), such that the longitudinal position of pin (210) is fixed relative to shaft (230). A pair of linear actuators (262, 264) are slidably disposed in shaft (230), and are pivotally coupled with arms (242, 244) by respective links (272, 274). In particular, link (272) is pivotally coupled with a proximal end (246) of arm (242) and is also pivotally coupled with linear actuator (262). Link (274) is pivotally coupled with a proximal end (248) of arm (244) and is also pivotally coupled with linear actuator (264). Linear actuators (262, 264) extend along the length of shaft (230) and are selectively translated by one or more features at handle portion (20). For instance, each linear actuator (262, 264) may be associated with a respective pivoting grip (24) via rack and pinion configurations, camming features, etc. Alternatively, linear actuators (262, 264) may be operated by sliders, motors, solenoids, or any other suitable driving components as will be apparent to those of ordinary skill in the art in view of the teachings herein. It should also be understood that actuators (262, 264) are operable independently relative to each other in the present example.

Needle (250) of this example includes a sharp tip (252) at one end and a suture (254) secured to the other end. Alternatively, both ends of needle (250) may include sharp tips, with suture (254) being secured in a middle region of needle (250) between the sharp tips. While needle (250) is curved in this example, some other versions may include use of a straight needle, an angled needle, or any other suitable type of needle.

Figure 12:
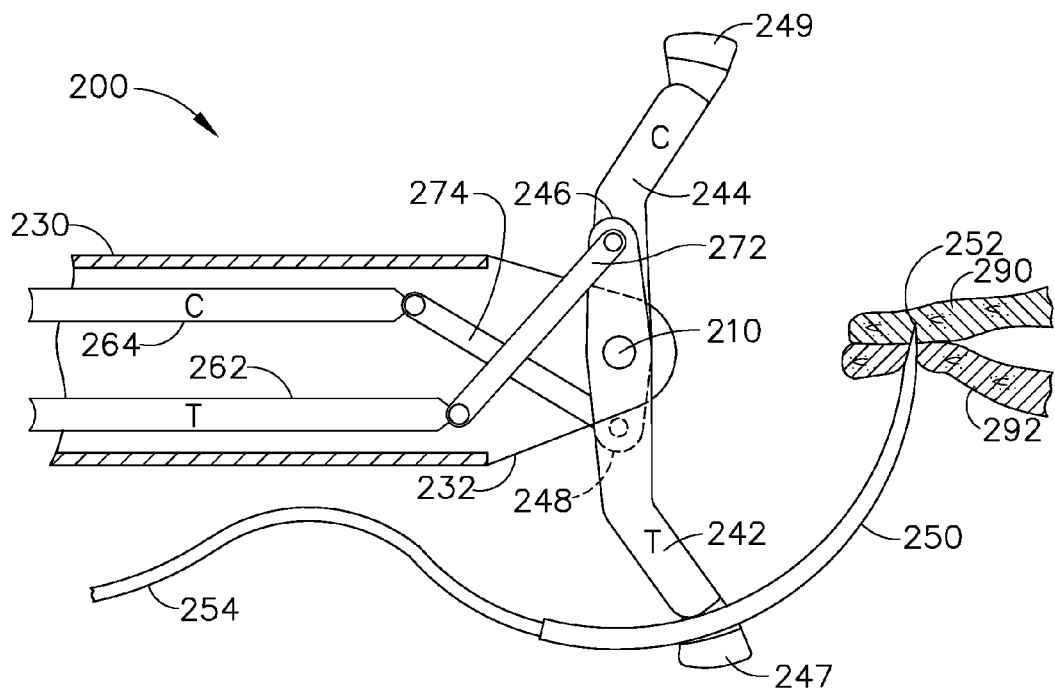
FIG. 12 depicts a partial, cross-sectional side view of another exemplary alternative end effector for a laparoscopic suturing device, in a first operational configuration.
Figure 13:
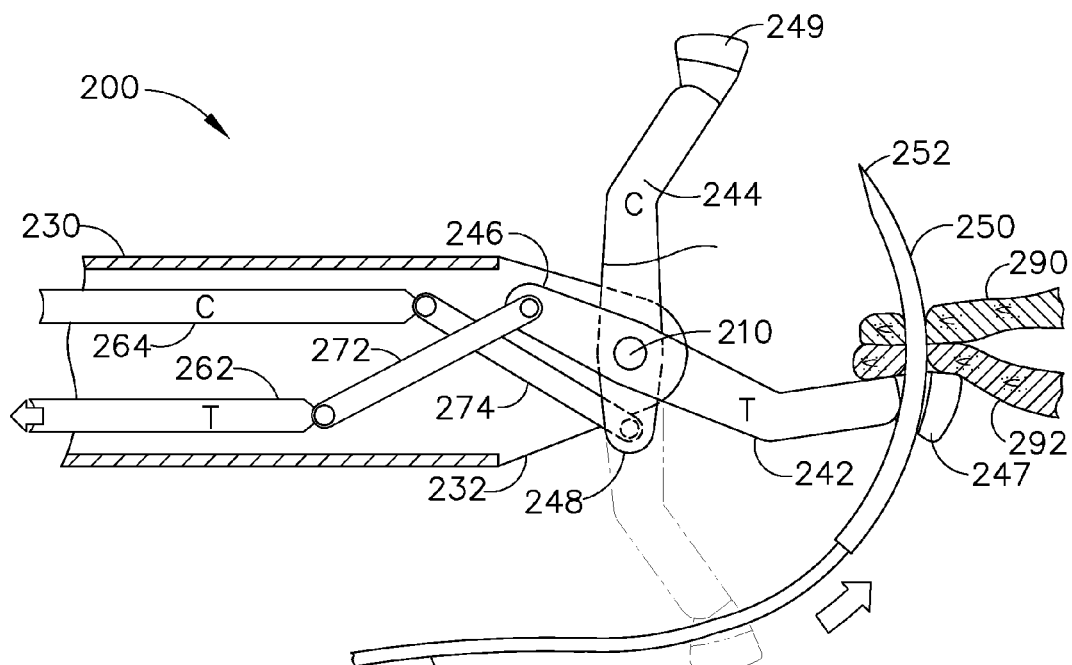
FIG. 13 depicts a partial, cross-sectional side view of the end effector of FIG. 12, in a second operational configuration.

In an exemplary method of operation, end effector (200) is positioned near two layers (190, 192) of tissue, as shown in FIG. 12. The user may move the entire shaft (230) and end effector (200) together to begin piercing the layers (290, 292) of tissue with sharp tip (252) of needle (250). Then, actuator (262) is retracted proximally to the position shown in FIG. 13. This proximal movement of actuator (262) causes link (272) to pull proximal end (246) of arm (242), which in turn pivots the distal end (247) of arm (242) into engagement with lower layer (292) of tissue and also drives needle (250) through both layers (290, 292) of tissue. Arm (244) remains substantially stationary during this stage since actuator (264) and link (274) are independent from actuator (262) and link (272). With arm (244) engaging lower layer (292) of tissue, actuator (264) is retracted proximally to the position shown in FIG. 14. This proximal movement of actuator (264) causes link (274) to pull proximal end (248) of arm (244), which in turn pivots the distal end (249) of arm (244) toward upper layer (290) of tissue.

Figure 14:
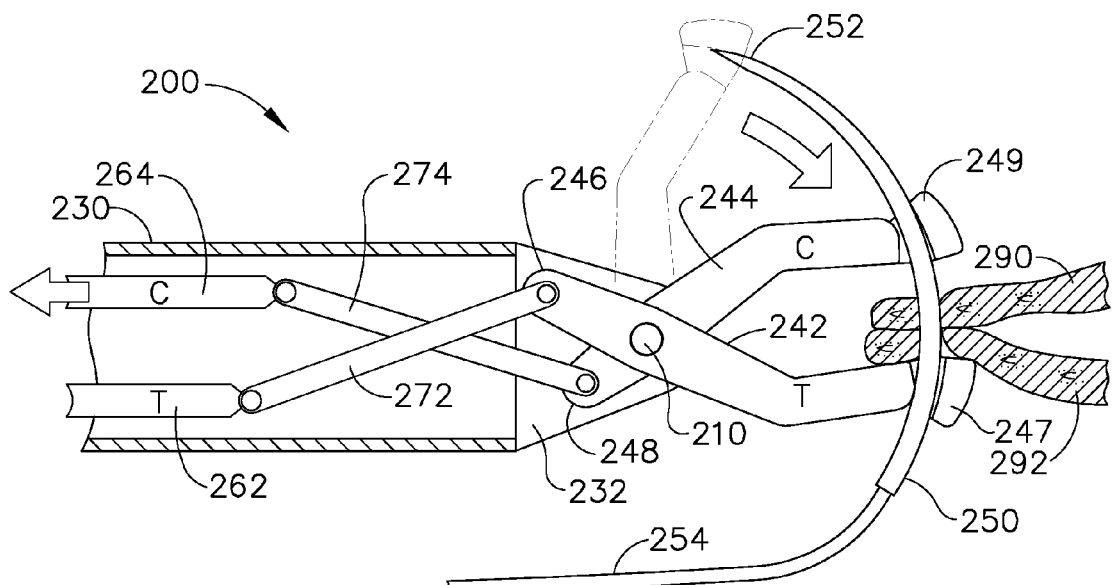
FIG. 14 depicts a partial, cross-sectional side view of the end effector of FIG. 12, in a third operational configuration.

With arms (242, 244) in the positions shown in FIG. 14, the user may then actuate button (26) or some other feature to release needle (250) from arm (242) and grip needle (250) with arm (244). Examples of various suitable components, features, and configurations that may be used to provide such selective gripping of needle (250) by arms (242, 244) are taught in U.S. Provisional Application Ser. No. 61/355,832, the disclosure of which is incorporated by reference herein. Still other suitable components, features, and configurations that may be used to provide selective gripping of needle (250) by arms (242, 244) will be apparent to those of ordinary skill in the art in view of the teachings herein. It should also be understood that needle (250) may also include features to facilitate selective gripping, including but not limited to one or more notches, etc.

Figure 15:
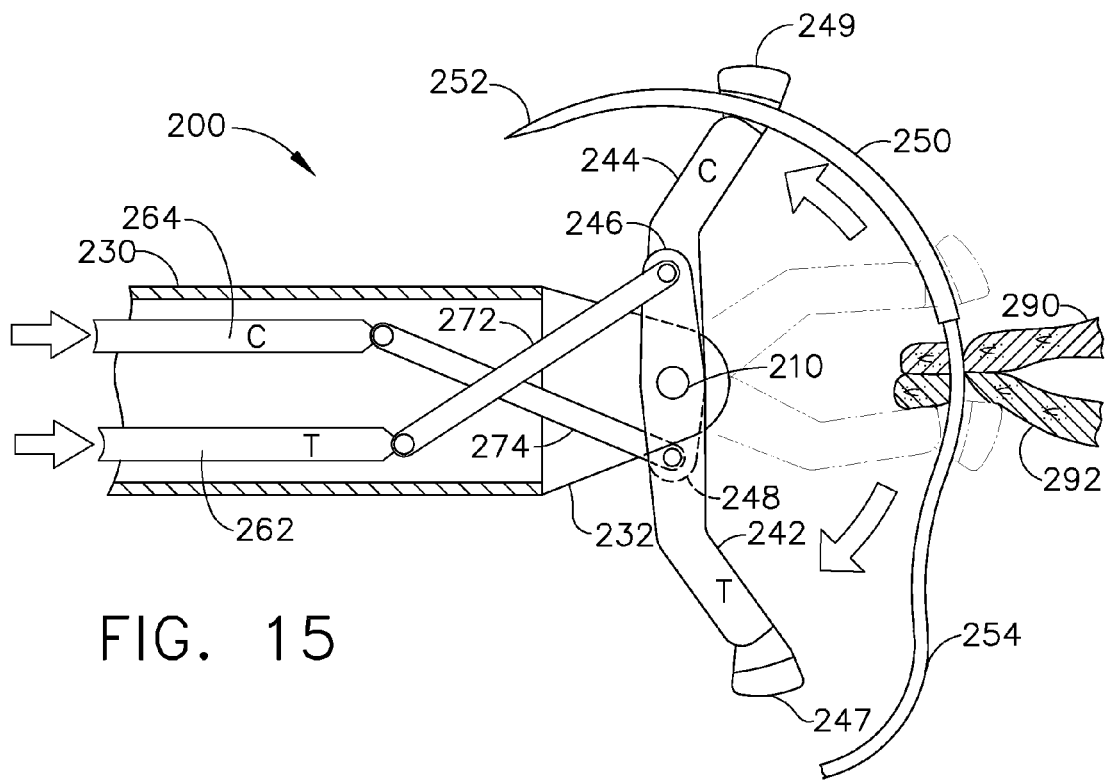
FIG. 15 depicts a partial, cross-sectional side view of the end effector of FIG. 12, in a fourth operational configuration.
Figure 16:
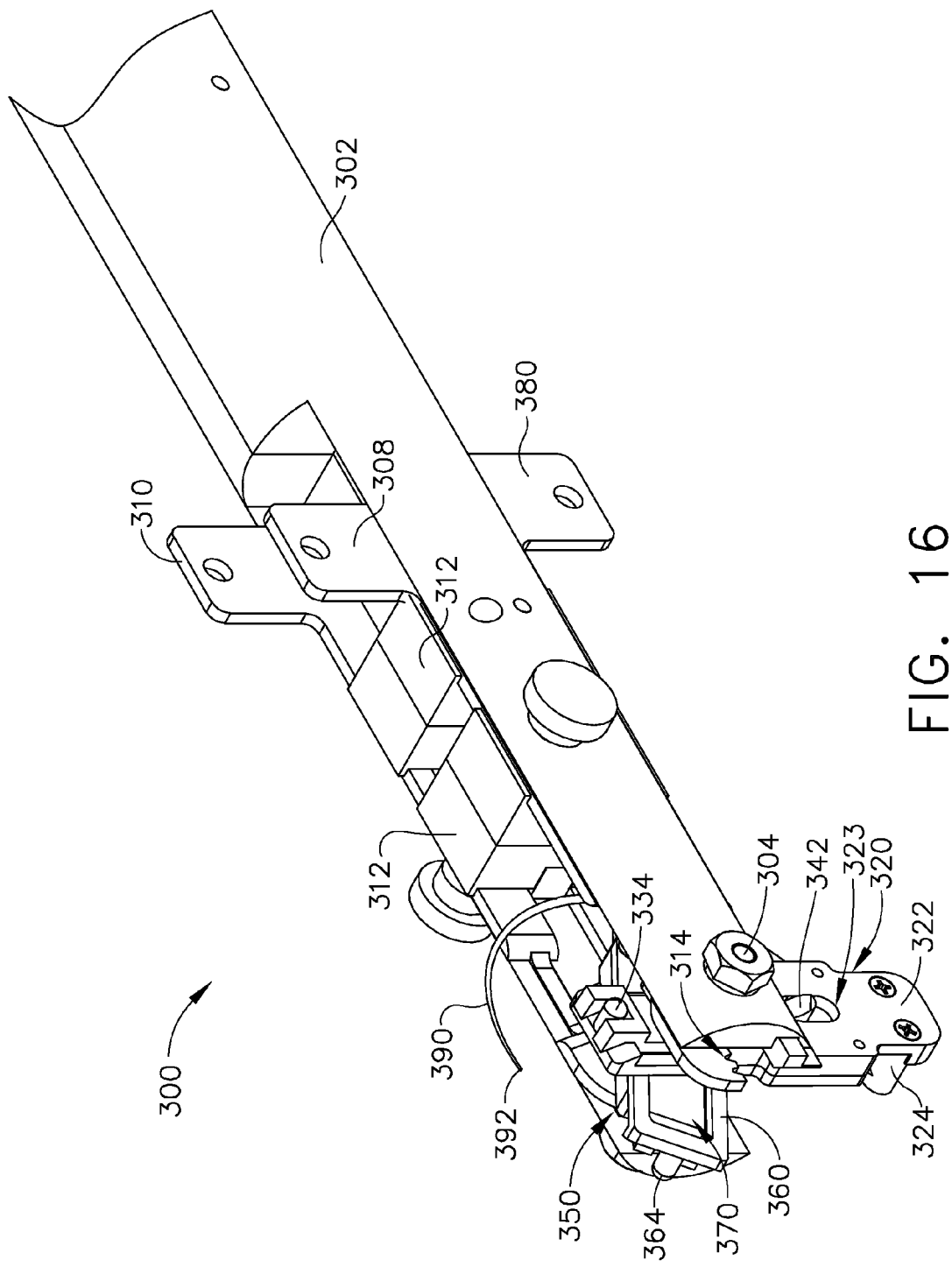
FIG. 16 depicts a perspective view of an exemplary alternative end effector for a laparoscopic suturing device, in a first operational configuration.
Figure 17:
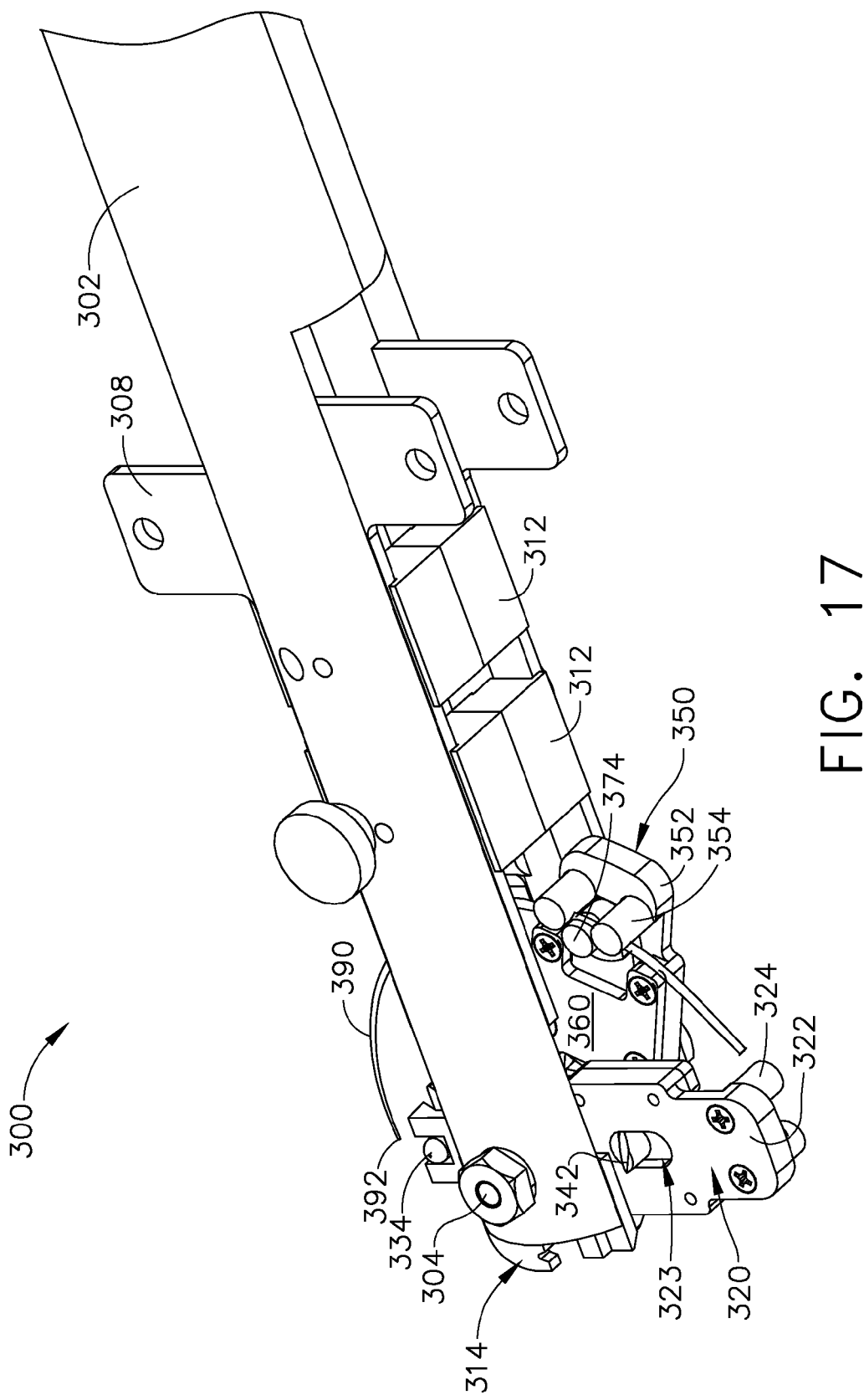
FIG. 17 depicts another perspective view of the end effector of FIG. 16, in the first operational configuration.

With needle (250) having been thrown by arm (242) through both layers (290, 292) of tissue, and with needle (250) having been caught by arm (244), the user may then release whatever features were used to translate actuators (262, 264) proximally. A resilient bias may then advance actuators (262, 264) distally, thereby pivoting arms (242, 244) back to their previous positions, as shown in FIG. 15. Alternatively, actuators (262, 264) may be actively advanced distally by the user (e.g., by pushing on a feature in handle portion (20), etc.). The movement of arm (244) away from the layers (290, 292) of tissue pulls needle (250) and suture (254) through both layers (290, 292) of tissue. The user may then pull end effector (200) away from layers (290, 292), to pull an additional length of suture (254) through layers (290, 292) and/or to tighten suture (254), if desired. Next, with arms (242, 244) positioned away from the surgical site, the user may again actuate actuators (262, 264) to pass needle (250) back to arm (242) in a "reverse reset" action as referred to above. Arms (242, 244) may then be positioned back at the surgical site, and the above process may be repeated until the desired number of stitches have been placed at the surgical site. The free end of the suture may then be knotted, clipped, or otherwise secured. In this example, arm (242) serves a dedicated role as the throwing arm each time needle (250) passes through layers (290, 292) of tissue; while arm (244) serves a dedicated role as the catching arm each time needle (250) passes through layers (290, 292) of tissue. In some such versions, shaft (230) is rotated 180° about its longitudinal axis before each time arm (242) drives needle (250) through tissue. It should also be understood that, in some versions where suture (254) is secured to one end of needle (250) as well as some versions where suture (254) is secured to the middle of needle (250), arms (242, 244) may alternate roles as throwing arm and catching arm. Other suitable ways in which end effector (200) may be used with such needles (250) will be apparent to those of ordinary skill in the art in view of the teachings herein.

While the series depicted in FIGS. 12-15 shows arm (242) contacting tissue before arm (244), it should be understood that a user may wish to contact tissue with arm (244) before contacting tissue with arm (242). For instance, the user may wish to use arm (244) to provide traction or an opposing force when needle (250) is driven through layers (290, 292) of tissue. With actuators (262, 264) being movable independently relative to each other, the user may actuate actuators (262, 264) and thus arms (242, 244) in any desired sequence or timing.

III. EXEMPLARY SUTURE DEVICE WITH DUAL AXLE DRIVE ASSEMBLY

A. Exemplary Drive Assembly with Oscillating Arms and Forward Needle Reset

FIGS. 16-28 depict another exemplary end effector (300) that may be incorporated into instrument (10) as an alternative to end effector (40) described above. It should also be understood that end effector (300) may be incorporated into various other instruments, such that end effector (300) is not limited to instrument (10). End effector (300) of this example is disposed at the distal end of a shaft (302) and includes a pair of arms (320, 350) that selectively throw and catch a needle (390). Each arm (320, 350) is secured to a respective axle (304, 306), and each arm (320, 350) pivotally rocks or oscillates about its respective axle (304, 306) as will be described in greater detail below. While axles (304, 306) are aligned along a common axis, axles (304, 306) are separate from each other such that a gap is defined between axles (304, 306), with that gap also lying along the common axis. Axles (304, 306) are pivotally secured to shaft (302). The axis along which axles (304, 306) are aligned and oscillate is perpendicular to a longitudinal axis defined by shaft (302). Thus, arms (320, 350) oscillate along respective planes that are parallel to the longitudinal axis defined by shaft (302) and that are parallel to each other. In the present example, arms (320, 350) also move asynchronously, such that one arm (320, 350) may remain stationary as the other arm (350, 320) is moving.

Figure 18:
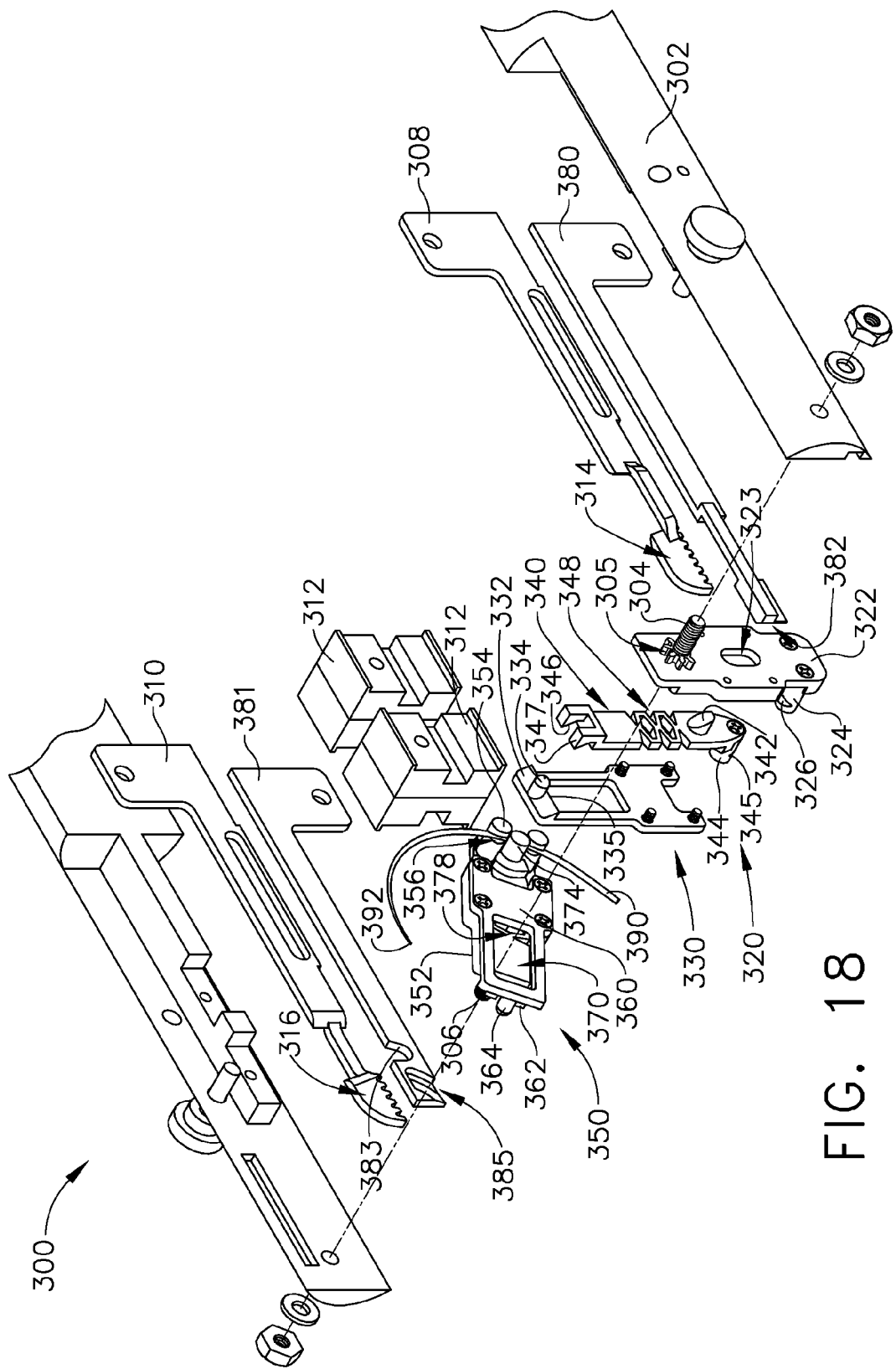
FIG. 18 depicts an exploded view of the end effector of FIG. 16.

A pair of arm rotation actuators (308, 310) are slidably disposed in shaft (302) and are laterally separated by spacer blocks (312). As best seen in FIG. 18, each arm rotation actuator (308, 310) includes a respective integral distal rack portion (314, 316). Each axle (304, 306) includes a respective integral pinion portion (305). While only pinion portion (305) of axle (304) is shown in FIG. 18, it should be understood that axle (306) has a similar pinion portion in the present example. Rack portions (314, 316) are engaged with pinion portions (305). Thus, longitudinal movement of arm rotation actuators (308, 310) provides corresponding rotation of pinion portions (305). Since pinion portions (305) are unitary with arms (320, 350), the rotational motion of pinion portions (305) provides corresponding rotation of arms (320, 350). In the present example, arms (320, 350) do not rotate through full revolutions, so rotation of arms (320, 350) will be described herein using terms such as "rocking" or "oscillation" and the like. It should be understood, however, that one or both of arms (320, 350) may rotate through full revolutions in some other versions. It should also be understood that arm rotation actuators (308, 310) may be driven in any suitable fashion, including but not limited to being driven by sliders, motors, solenoids, or any other suitable driving components as will be apparent to those of ordinary skill in the art in view of the teachings herein. Furthermore, it should be understood that arm rotation actuators (308, 310) are operable independently relative to each other in the present example.

Arm (320) of the present example includes a first frame member (322), a second frame member (330), and a needle gripping member (340). First frame member (322) is unitary with axle (304) and pinion portion (305). First frame member (322) includes a pair of transversely extending needle gripping pegs (324). Each needle gripping peg (324) includes a respective notch (326) that is configured to receive part of needle (390) as first frame member (322) cooperates with needle gripping member (340) to selectively grip needle (390). Notches (326) are configured to assist in properly aligning needle (390) as needle (390) is being gripped by arm (320), such as if/when needle (390) twists or otherwise changes orientation as needle (390) is being passed through tissue.

Second frame member (330) is fixedly secured to first frame member (322). Second frame member (330) includes an angled surface (332) and a transversely extending deflection peg (334). An engagement surface (335) is adjacent to angled surface (332). As will be described in greater detail below, deflection peg (334) may be pushed during operation of end effector (300), to push angled surface (332) and engagement surface (335) away from first frame member (322). Second frame member (330) is resilient and thus flexes to permit such deflection in the present example. However, second frame member (330) is resiliently biased to maintain a substantially straight orientation that is parallel to first frame member (322).

Needle gripping member (340) is sandwiched between first frame member (322) and second frame member (330). Needle gripping member (340) is also slidable between first frame member (322) and second frame member (330), as will be described in greater detail below. Needle gripping member (340) comprises a transversely extending cam peg (342), a transversely extending needle gripping peg (344), a pair of angled surfaces (346), and a flex portion (348). A pair of engagement surfaces (347) are adjacent to angled surfaces (346). Cam peg (342) is disposed through a slot (323) formed in first frame member (322). Needle gripping peg (344) includes a notch (345) that is configured to receive part of needle (390) as first frame member (322) cooperates with needle gripping member (340) to selectively grip needle (390). Notches (345, 326) cooperate to properly align needle (390) as needle (390) is being gripped by arm (320), such as if/when needle (390) twists or otherwise changes orientation as needle (390) is being passed through tissue. Flex portion (348) allows needle gripping member (340) to compress along a longitudinal axis defined by needle gripping member (340); yet flex portion (348) resiliently biases needle gripping member (340) to the longitudinally extended position shown in FIGS. 16-18, 20-22, and 28.

Figure 23A:
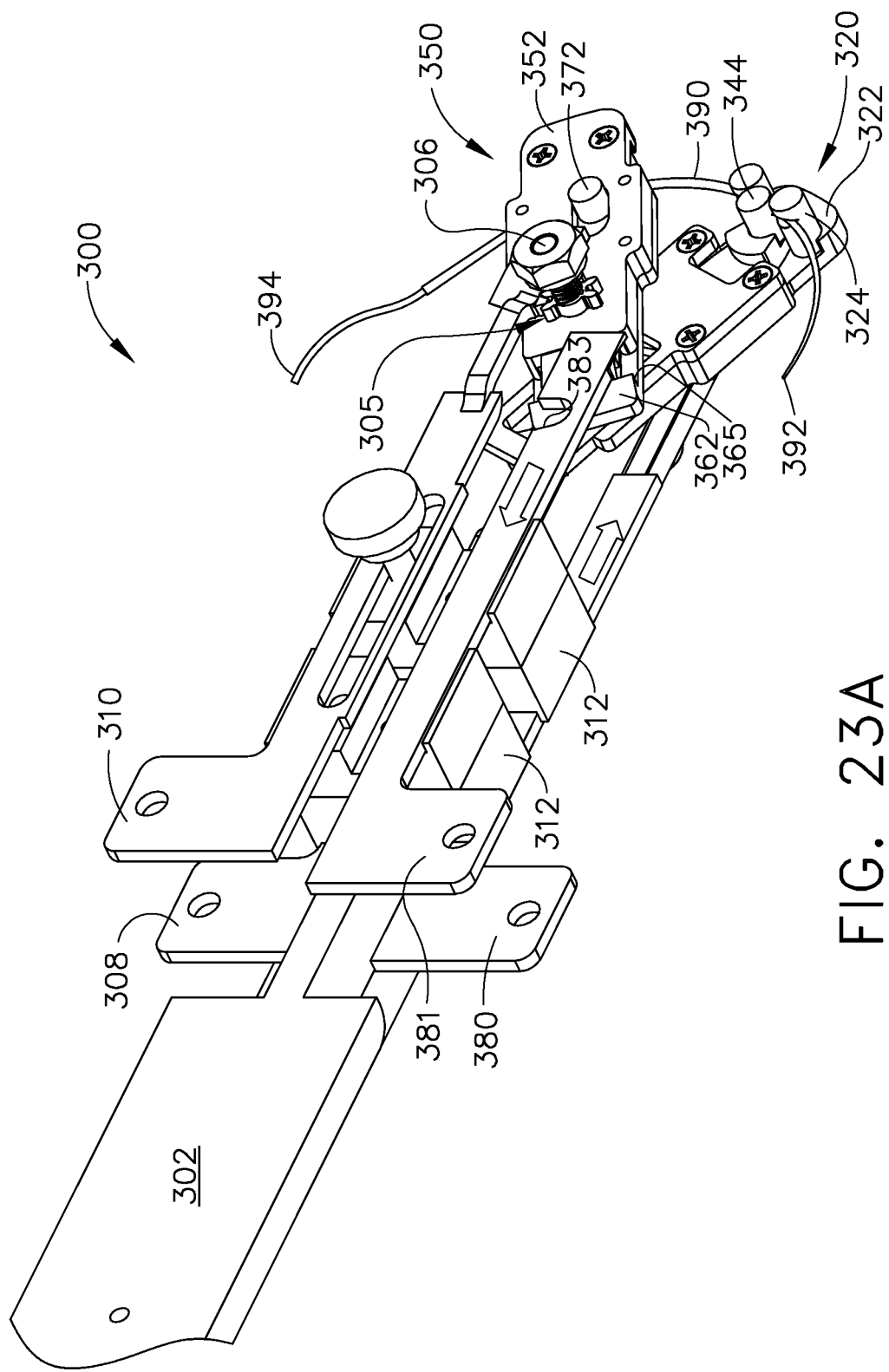
FIG. 23A depicts a partial perspective view of the end effector of FIG. 16, in a fourth operational configuration.
Figure 23B:
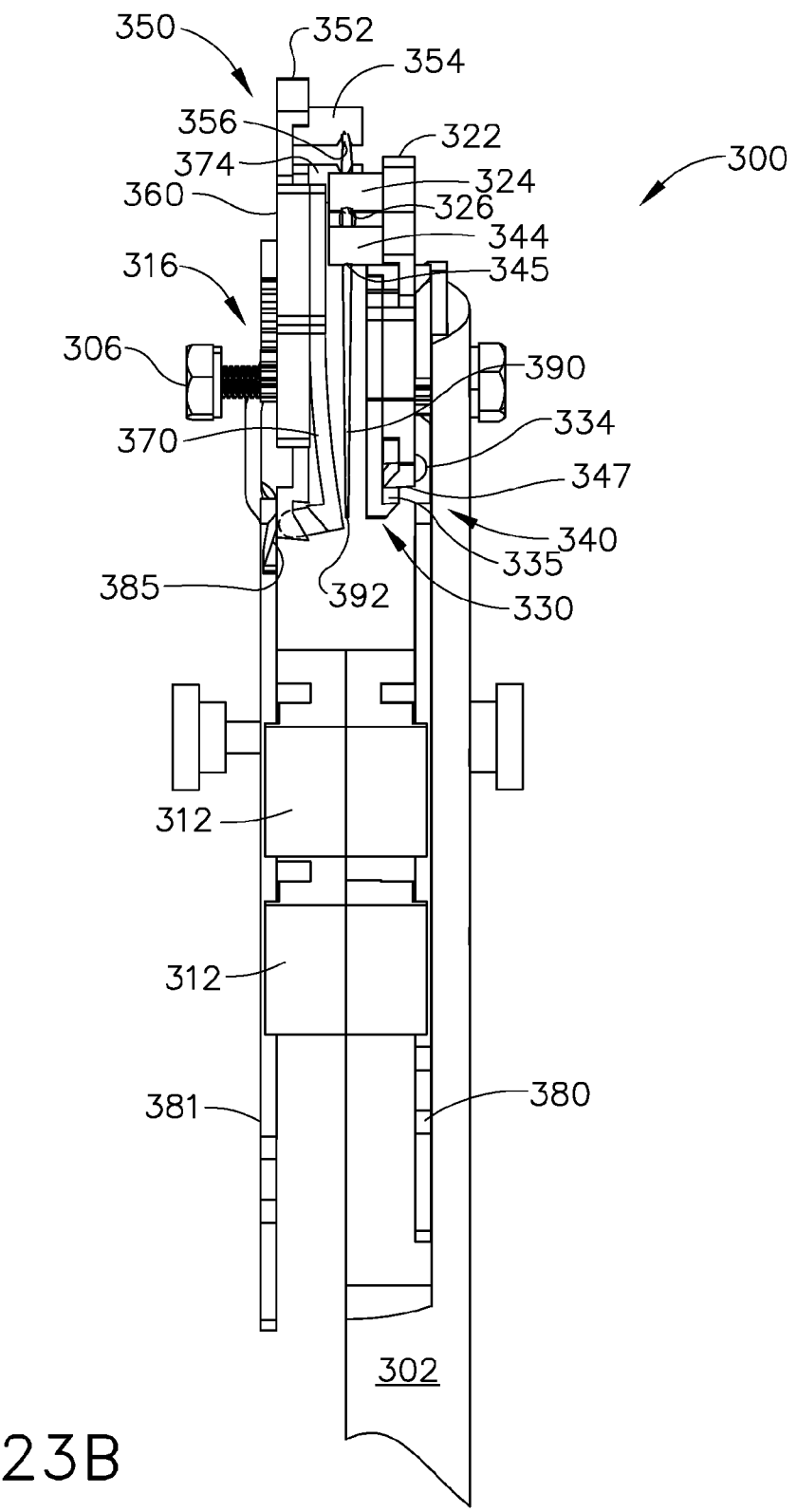
FIG. 23B depicts a partial, bottom plan view of the end effector of FIG. 16, in the fourth operational configuration.
Figure 27:
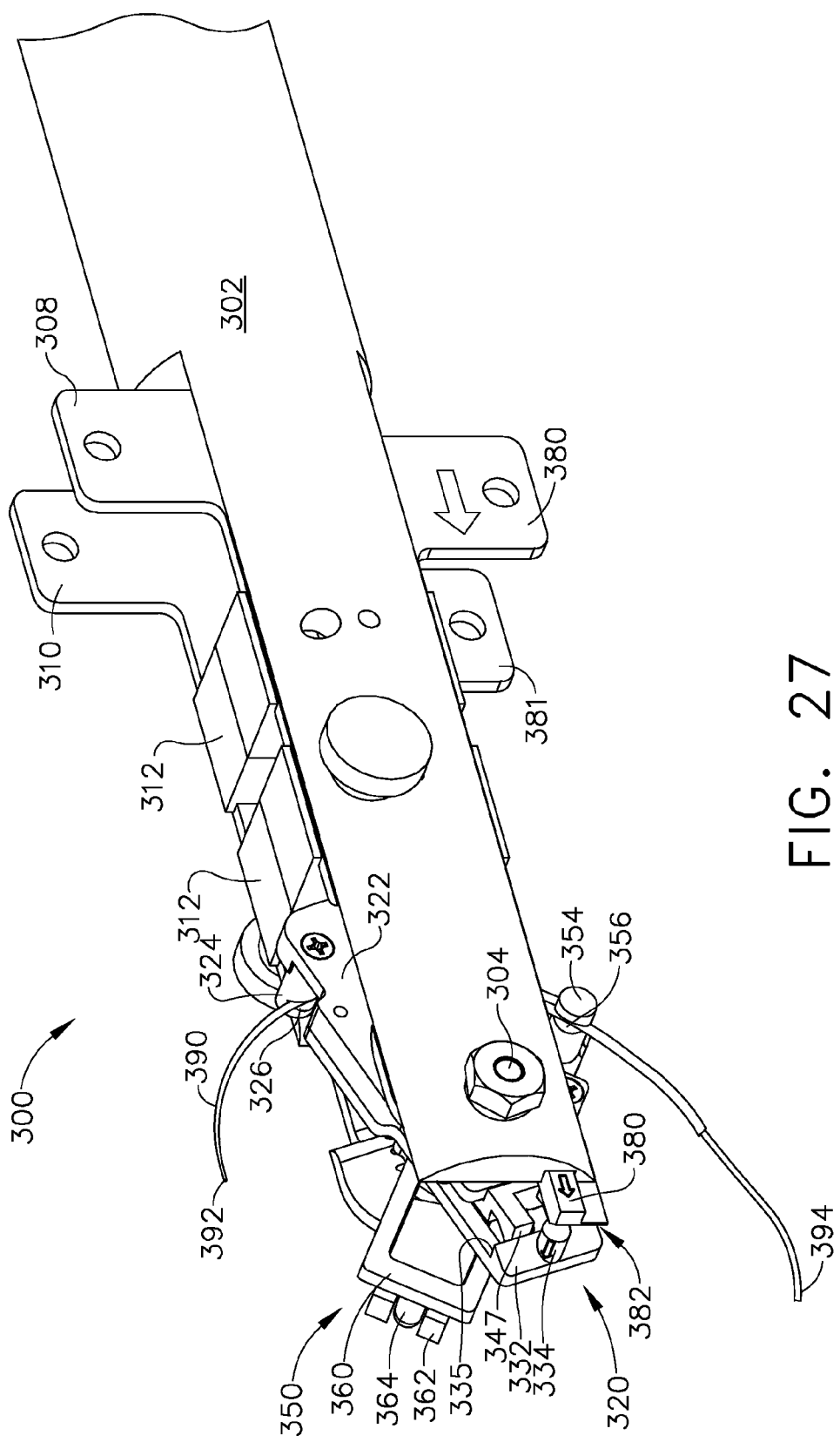
FIG. 27 depicts a perspective view of the end effector of FIG. 16, in an eighth operational configuration.
Figure 28:
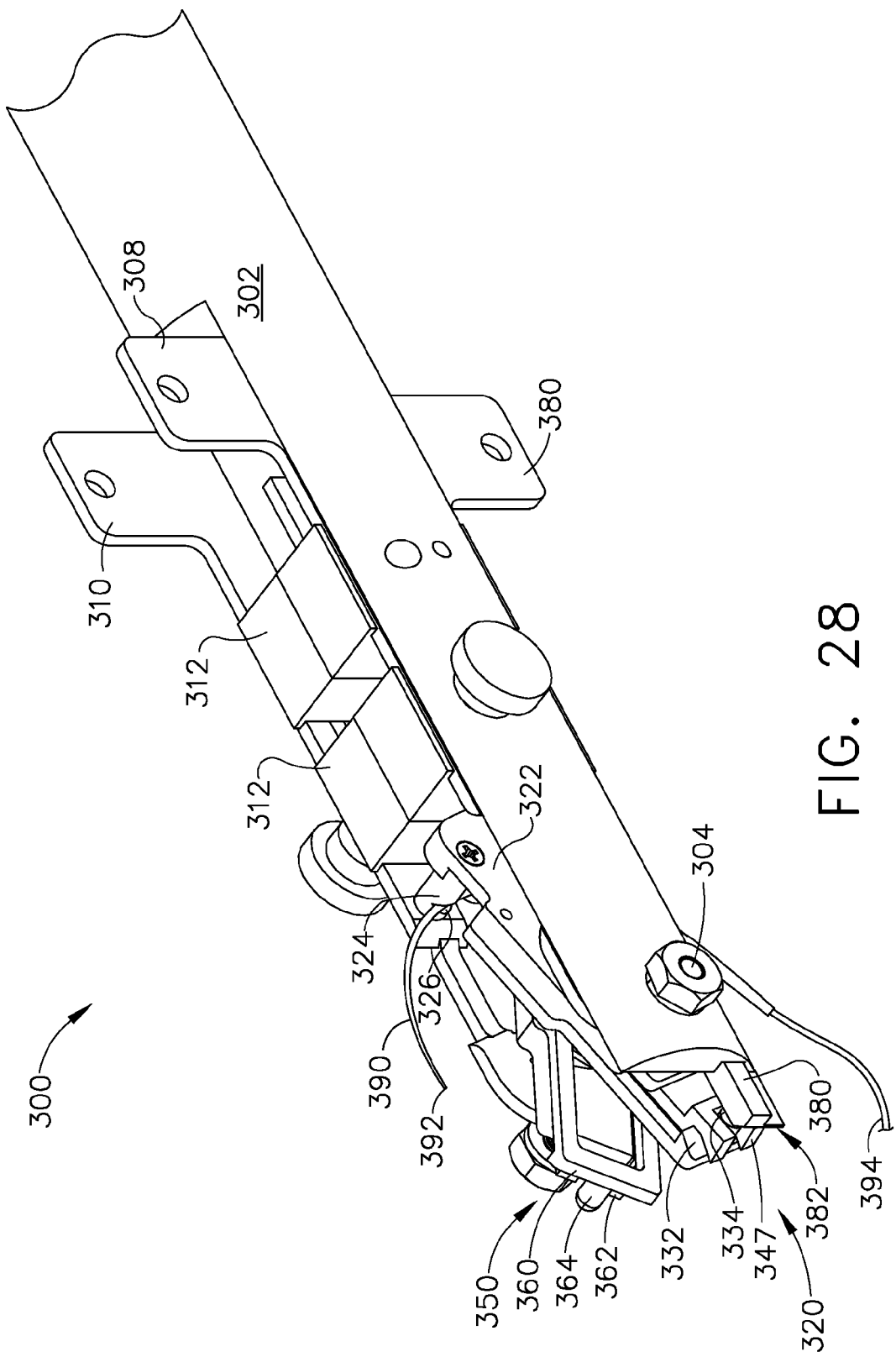
FIG. 28 depicts a perspective view of the end effector of FIG. 16, in a ninth operational configuration.

A cam actuator (380) is slidably disposed in shaft (302) and includes a chamfered distal end portion (382) that is operable to selectively engage cam peg (342). Chamfered distal end portion (382) of cam actuator (380) is also operable to selectively engage deflection peg (334). For instance, as shown in FIGS. 23A-23B and as will be described in greater detail below, cam actuator (380) may push on cam peg (342) when cam actuator (380) is driven to a distal position with arm (320) at a particular distal rotational position, thereby sliding needle gripping member (340) to a needle gripping position and configuration. In addition, as shown in FIGS. 27-28 and as will be described in greater detail below, cam actuator (380) may push on deflection peg (334) when cam actuator (380) is driven to a distal position with arm (320) at a particular proximal rotational position, thereby allowing needle gripping member (340) to transition from a needle gripping position and configuration to a needle releasing position and configuration. Cam actuator (380) may be driven manually by a slider, may be driven by a motor or solenoid, or may be driven in any other suitable fashion as will be apparent to those of ordinary skill in the art in view of the teachings herein. It should also be understood that cam actuator (380) may be driven independently relative to arm rotation actuator (308).

Arm (350) of the present example includes a first frame member (352), a second frame member (360), and a needle gripping member (370). First frame member (352) is unitary with axle (306) and pinion portion (not shown). First frame member (352) includes a pair of transversely extending needle gripping pegs (354). Each needle gripping peg (354) includes a respective notch (356) that is configured to receive part of needle (390) as first frame member (362) cooperates with needle gripping member (370) to selectively grip needle (390). Notches (356) are configured to assist in properly aligning needle (390) as needle (390) is being gripped by arm (350), such as if/when needle (390) twists or otherwise changes orientation as needle (390) is being passed through tissue.

Second frame member (360) is fixedly secured to first frame member (352). Second frame member (360) includes an angled surface (362) and a transversely extending deflection peg (364). An engagement surface (365) is adjacent to angled surface (362). As will be described in greater detail below, deflection peg (364) may be pushed during operation of end effector (300), to push angled surface (362) and engagement surface (365) away from first frame member (352). Second frame member (360) is resilient and thus flexes to permit such deflection in the present example. However, second frame member (360) is resiliently biased to maintain a substantially straight orientation that is parallel to first frame member (352).

Needle gripping member (370) is sandwiched between first frame member (352) and second frame member (360). Needle gripping member (370) is also slidable between first frame member (352) and second frame member (360), as will be described in greater detail below. Needle gripping member (370) comprises a transversely extending cam peg (372), a transversely extending needle gripping peg (374), a pair of angled surfaces (376), and a flex portion (378). A pair of engagement surfaces (377) are adjacent to angled surfaces (376). Cam peg (372) is disposed through a slot (353) formed in first frame member (352). Needle gripping peg (374) includes a notch (not shown) that is configured to receive part of needle (390) as first frame member (352) cooperates with needle gripping member (370) to selectively grip needle (390). This notch of needle gripping peg (374) cooperates with (356) of first frame member (352) to properly align needle (390) as needle (390) is being gripped by arm (350), such as if/when needle (390) twists or otherwise changes orientation as needle (390) is being passed through tissue. Flex portion (378) allows needle gripping member (370) to compress along a longitudinal axis defined by needle gripping member (370), yet flex portion (378) resiliently biases needle gripping member (370) to the longitudinally extended position shown in FIGS. 24-25.

Figure 19:
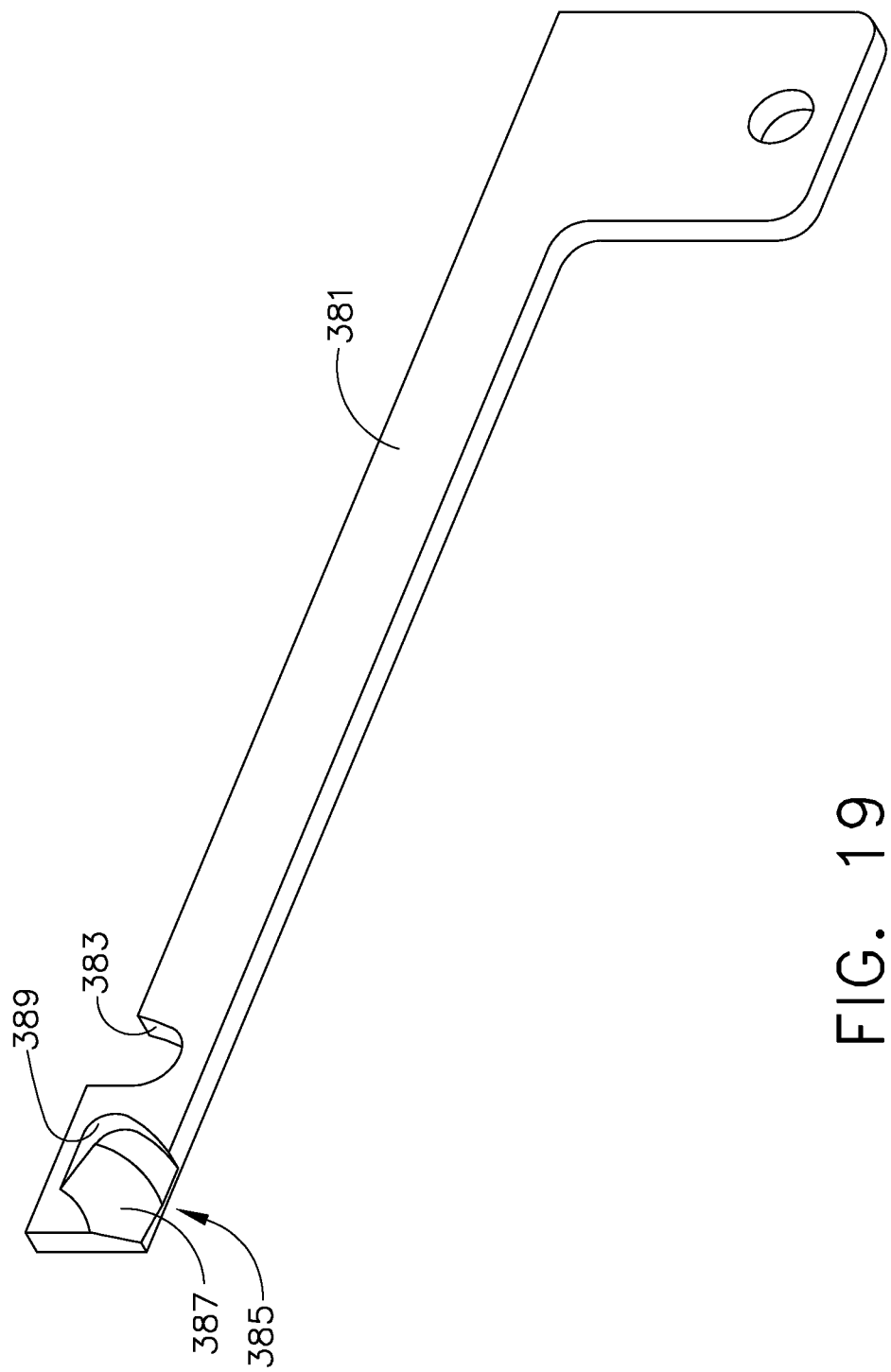
FIG. 19 depicts a perspective view of an actuating member of the end effector of FIG. 16.
Figure 20:
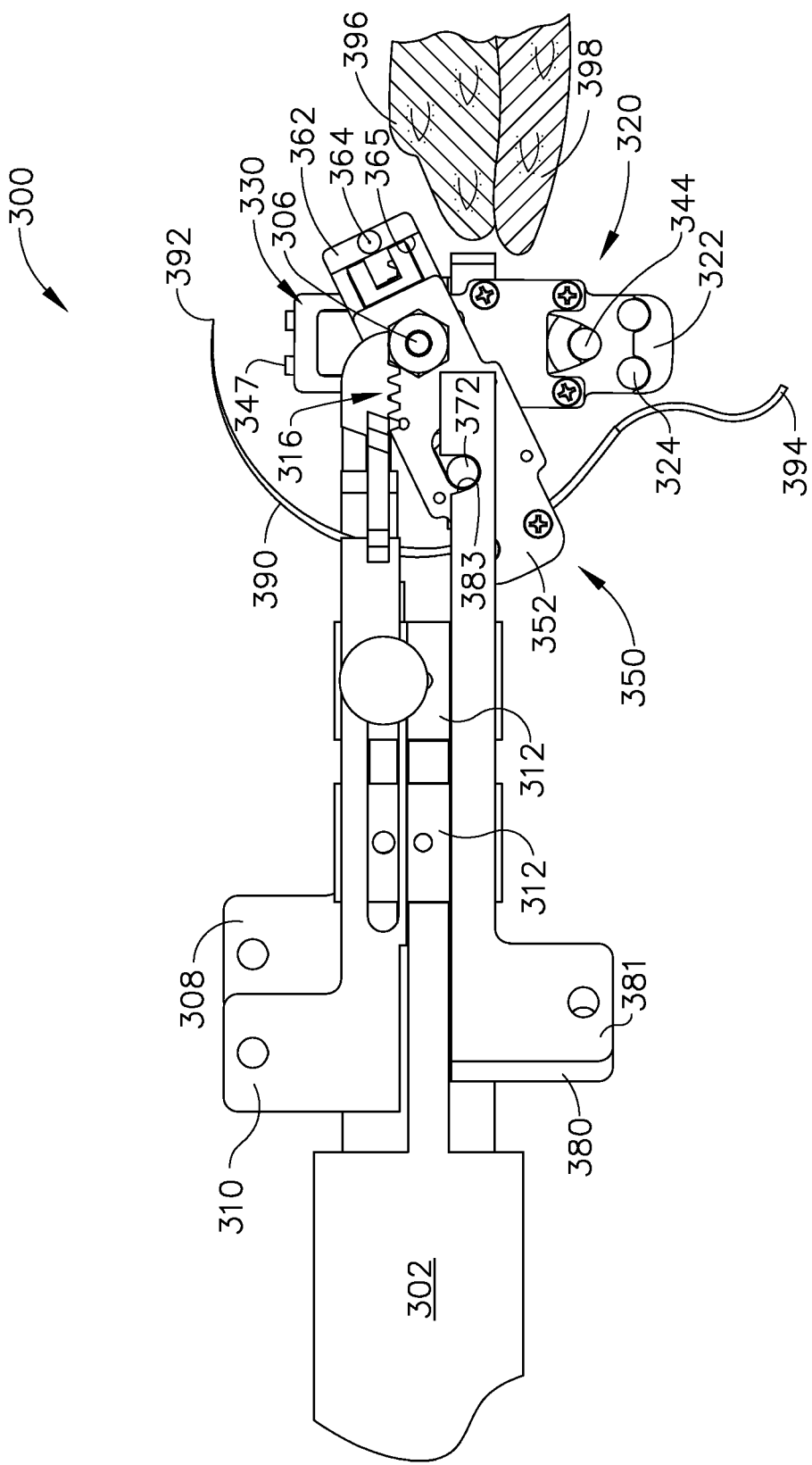
FIG. 20 depicts a partial, cross-sectional side view of the end effector of FIG. 16, in the first operational configuration.
Figure 22:
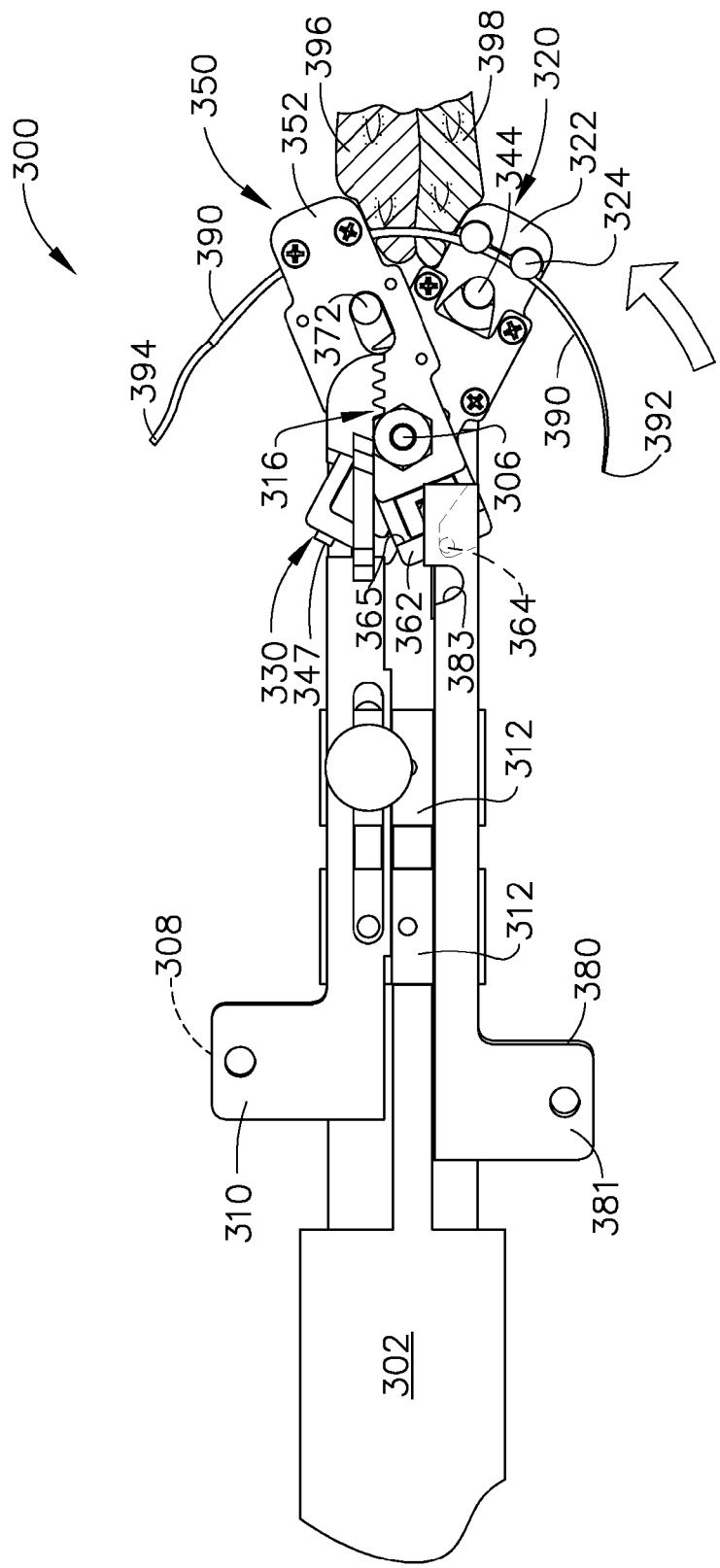
FIG. 22 depicts a partial, cross-sectional side view of the end effector of FIG. 16, in a third operational configuration.

A cam actuator (381) is slidably disposed in shaft (302). As best seen in FIG. 19, cam actuator (381) of this example includes a lateral notch (383) and a distal recess (385). Distal recess (385) is defined by an angled lateral surface (387) and a proximal surface (389). Lateral notch (383) is configured to selectively engage cam peg (372). In particular, as shown in FIG. 20 and as will be described in greater detail below, lateral notch (383) receives cam peg (372) during proximal rotation of arm (350) and thereby assists in arresting further proximal rotation of arm (350). Distal recess (385) is configured to selectively engage deflection peg (364). In particular, as shown in FIG. 22 and as will be described in greater detail below, proximal surface (389) engages deflection peg (364) during distal rotation of arm (350) and thereby assists in arresting further distal rotation of arm (350). Furthermore, as shown in FIGS. 23A-23B and as will also be described in greater detail below, angled lateral surface (387) may push on deflection peg (334) when actuator (381) is retracted to a proximal position with arm (350) at a particular distal rotational position, thereby allowing needle gripping member (370) to transition from a needle gripping position and configuration to a needle releasing position and configuration.

Needle (390) of this example includes a sharp tip (392) at one end and a suture (394) secured to the other end. Alternatively, both ends of needle (390) may include sharp tips, with suture (394) being secured in a middle region of needle (390) between the sharp tips. While needle (390) is curved in this example, some other versions may include use of a straight needle, an angled needle, or any other suitable type of needle.

In an exemplary method of operation, end effector (300) is positioned near two layers (396, 398) of tissue, as shown in FIG. 20. At this stage, needle (390) is gripped by pegs (354, 374) of arm (350). In particular, needle gripping member (370) is positioned such that engagement surfaces (377) of gripping member (370) are engaged with engagement surface (365) of second frame member (360). This relationship holds gripping member (370) in a position relative to frame members (352, 362) whereby needle gripping peg (374) is positioned near needle gripping pegs (354). In addition, flex portion (378) is compressed and provides a resilient bias to needle gripping peg (374), such that needle (390) remains held by pegs (354, 374) until gripping member (370) is slid relative to frame members (352, 360) during subsequent operation of end effector (300) as will be described in greater detail below.

Figure 21:
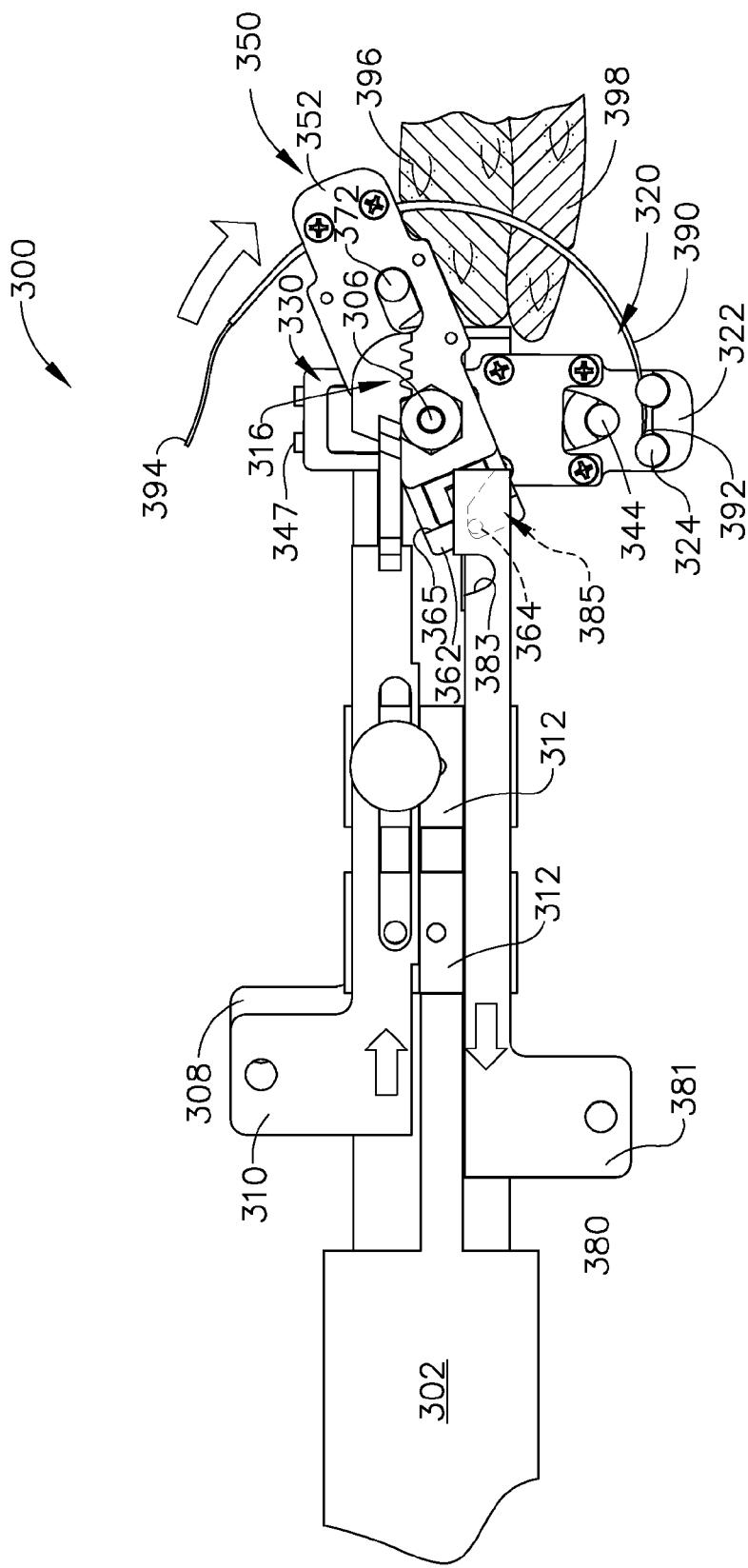
FIG. 21 depicts a partial, cross-sectional side view of the end effector of FIG. 16, in a second operational configuration.

With end effector (300) positioned near layers (396, 398) of tissue, and with needle (390) being held by pegs (354, 374) of arm (350), the user may translate actuator (310) distally as shown in FIG. 21. This distal motion of actuator (310) causes arm (350) to rotate forward, due to engagement between rack portion (316) of actuator (310) and pinion portion (305) of arm (350). The forward rotation of arm (350) causes sharp tip (392) of needle (390) to pierce and penetrate both layers (396, 398) of tissue. As also shown in FIG. 21, actuator (381) is translated proximally, positioning recess (385) to receive deflection peg (364). Thus, proximal surface (389) in recess (385) helps arrest further distal rotation of arm (350) by engaging peg (364). Arm (320) remains substantially stationary at this stage. Needle gripping pegs (324, 344) of arm (320) are positioned apart at this stage, such that arm (320) may freely receive needle (390). In some versions, arm (320) may be rotated to engage lower layer (398) of tissue to assist in clamping or providing ground against the tissue as needle (390) is inserted through layers (396, 398) of tissue at this stage. For instance, arm (320) may be rotated to the position shown in FIG. 22 as described in greater detail below, before arm (350) is rotated to the position shown in FIG. 21 as described above.

With needle (390) disposed in layers (396, 398) of tissue, and with needle (390) still being held by pegs (354, 374) of arm (350), the user may translate actuator (308) proximally to rotate arm (320) as shown in FIG. 22. Again, this translation of actuator (310) results in rotation of arm (320) through interaction between rack portion (314) of actuator (308) and pinion portion (305) of arm (320). Arm (320) is engaged against lower layer (398) of tissue, such that both layers (396, 398) of tissue are compressed between arms (320, 350) at this stage. In addition, needle gripping pegs (324, 344) of arm (320) remain positioned apart at this stage, such that arm (320) freely receives needle (390).

With needle (390) still disposed in layers (396, 398) of tissue, and with arm (320) in a position to receive needle (390), actuators (380, 381) are translated to transfer control of needle (390) from arm (350) to arm (320) as shown in FIGS. 23A-23B. In particular, as shown in FIG. 23A, actuator (380) is translated distally. This drives distal end portion (382) of actuator (380) into cam peg (342). Such pushing of cam peg (342) slides needle gripping member (340) relative to frame members (322, 330) of arm (320), bringing needle gripping peg (344) closer to needle gripping pegs (324) such that needle (390) is received in notches (326, 345) of pegs (324, 344). In addition, this sliding of needle gripping member (340) causes engagement surface (347) to snap into place in contact with engagement surface (335) of frame member (330). With engagement surfaces (335, 347) in contact with each other, needle gripping member (340) is held in the position shown in FIG. 23A. In this position, flex portion (348) is compressed, providing a resilient bias to needle gripping peg (344). This resilient bias helps to keep needle (390) gripped by pegs (324, 344) until gripping member (340) is slid relative to frame members (322, 330) during subsequent operation of end effector (300) as will be described in greater detail below.

As noted above, actuator (381) is translated proximally to release needle (390) from arm (350). In particular, when actuator (381) is translated proximally with arm (350) in the rotational position shown in FIGS. 23A-23B, angled lateral surface (387) of distal recess (385) pushes against deflection peg (364). This pushing against deflection peg (364) deforms frame member (360) to a point where engagement surface (377) clears engagement surface (365). Once engagement surface (377) clears engagement surface (365), the resilient bias of flex portion (378) causes gripping member (370) to extend in length. This extension in length helps cause gripping member (370) to slide relative to frame members (352, 360). In addition, angled surface (362) of frame member (360) interacts with angled surface (376) of gripping member (370) to further cause gripping member (370) to slide relative to frame members (352). With gripping member (370) being slid to the position shown in FIG. 23B, peg (374) has substantially separated from pegs (354), such that arm (350) has released needle (390).

In the present example, arm (350) does not release needle (390) until arm (320) has grasped needle (390). In other words, actuator (380) is translated distally first, then actuator (381) is translated proximally in the stages shown in FIGS. 23A-23B. In some other versions, arm (350) releases needle (390) simultaneously as arm (320) grasps needle (390), such that actuators (380, 381) are translated simultaneously.

Figure 24:
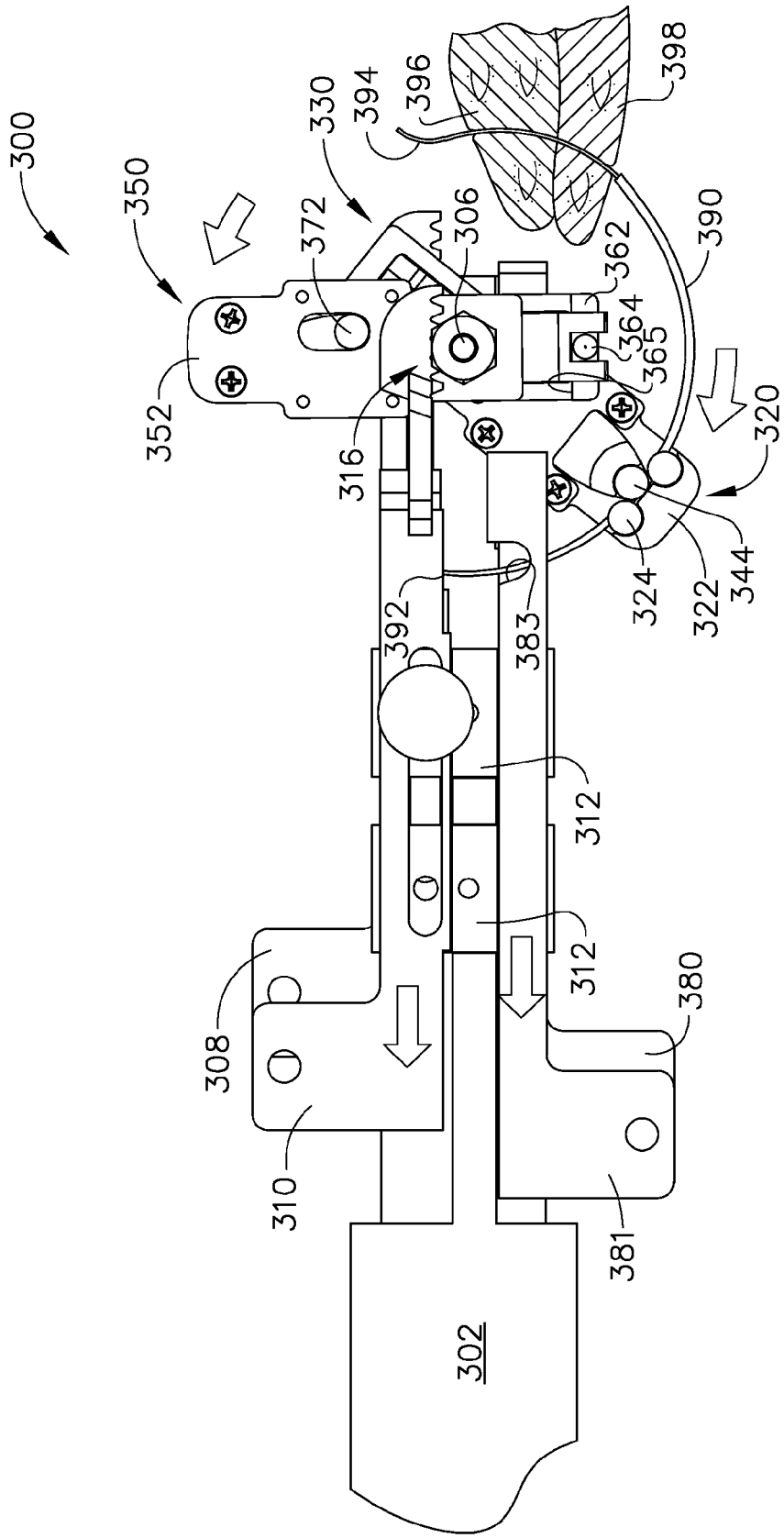
FIG. 24 depicts a partial, cross-sectional side view of the end effector of FIG. 16, in a fifth operational configuration.

With arm (320) having grasped needle (390) and with arm (350) having released needle (390), arm (322) is further rotated proximally to pull needle (390) free of layers (396, 398) of tissue and to pull suture (394) through layers (396, 398) of tissue as shown in FIG. 24. This is accomplished by translating actuator (308) distally. In addition, as also shown in FIG. 24, actuator (310) is translated proximally to rotate arm (350) proximally. While arms (320, 350) rotate simultaneously at this stage in the present example, it should be understood that arms (320, 350) may instead rotate in a staggered fashion or otherwise. Actuator (381) is also translated proximally at this stage in the present example. This proximal movement of actuator (381) allows cam peg (372) to clear actuator (381) as arm (350) continues to rotate proximally during subsequent stages of operation of end effector (300) as will be described in greater detail below.

Figure 25:
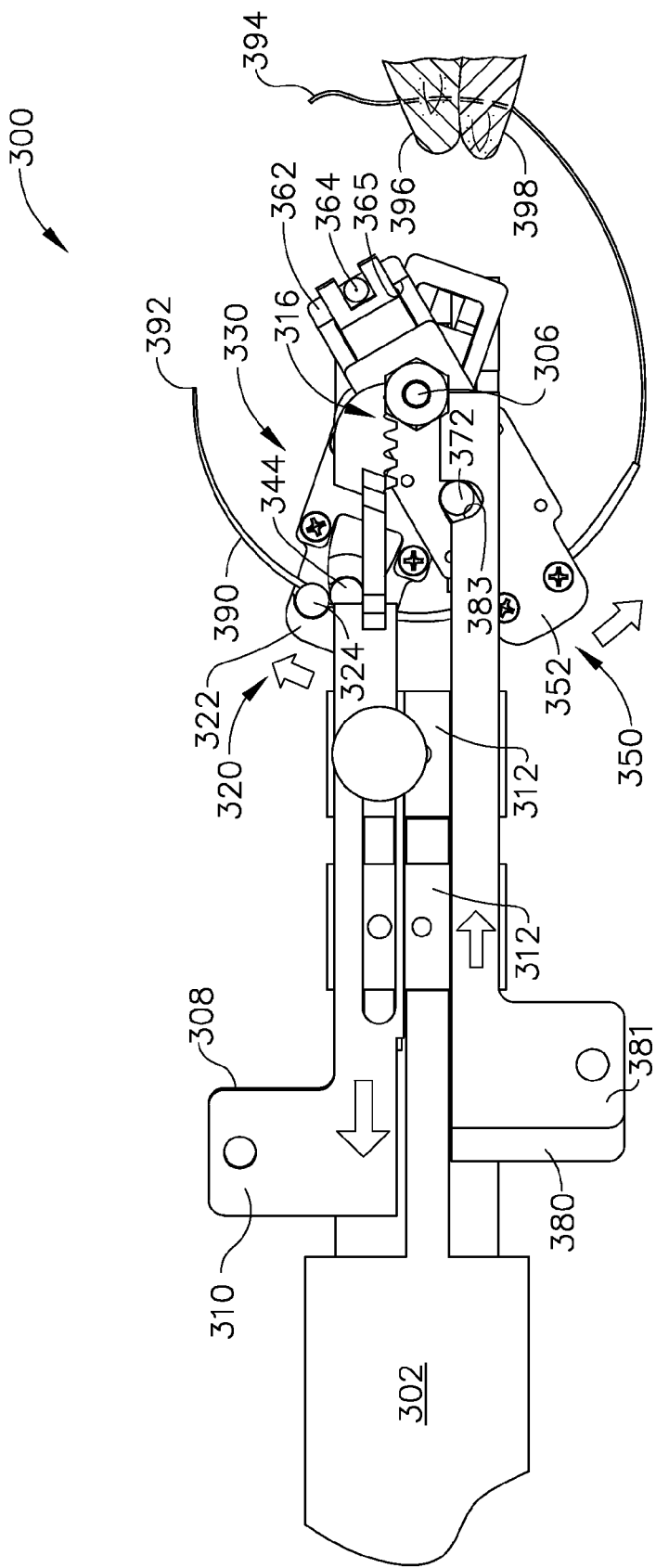
FIG. 25 depicts a partial, cross-sectional side view of the end effector of FIG. 16, in a sixth operational configuration.

As shown in FIG. 25, end effector (300) is then moved away from layers (396, 398) of tissue to tension suture (394); and arms (320, 350) are rotatably positioned to transfer needle (390) from arm (320) back to arm (350). In particular, actuator (310) is translated further proximally in order to rotate arm (350) to the position shown in FIG. 25. Actuator (308) is translated further distally in order to rotate arm (320) to the position shown in FIG. 25. Actuator (381) is translated distally to position lateral notch (383) at a location where it receives cam peg (372) to arrest further rotation of arm (350). At this stage, needle gripping pegs (324, 344) of arm (320) continue to grip needle (390); while needle gripping pegs (354, 374) of arm (350) are positioned apart to freely receive needle (390). It should be understood that, in the present example, arms (320, 350) move past each other during the transition between the configuration shown in FIG. 24 and the configuration shown in FIG. 25. In some instances, one or more pegs (354, 374) of arm (350) deflect relative one or more corresponding pegs (324, 344) of arm (350), such that pegs (324, 344, 354, 374) to not create a mechanical interference when arms (320, 350) move past each other during the transition between the configuration shown in FIG. 24 and the configuration shown in FIG. 25. Various other suitable ways of avoiding interferences will be apparent to those of ordinary skill in the art in view of the teachings herein.

Figure 26:
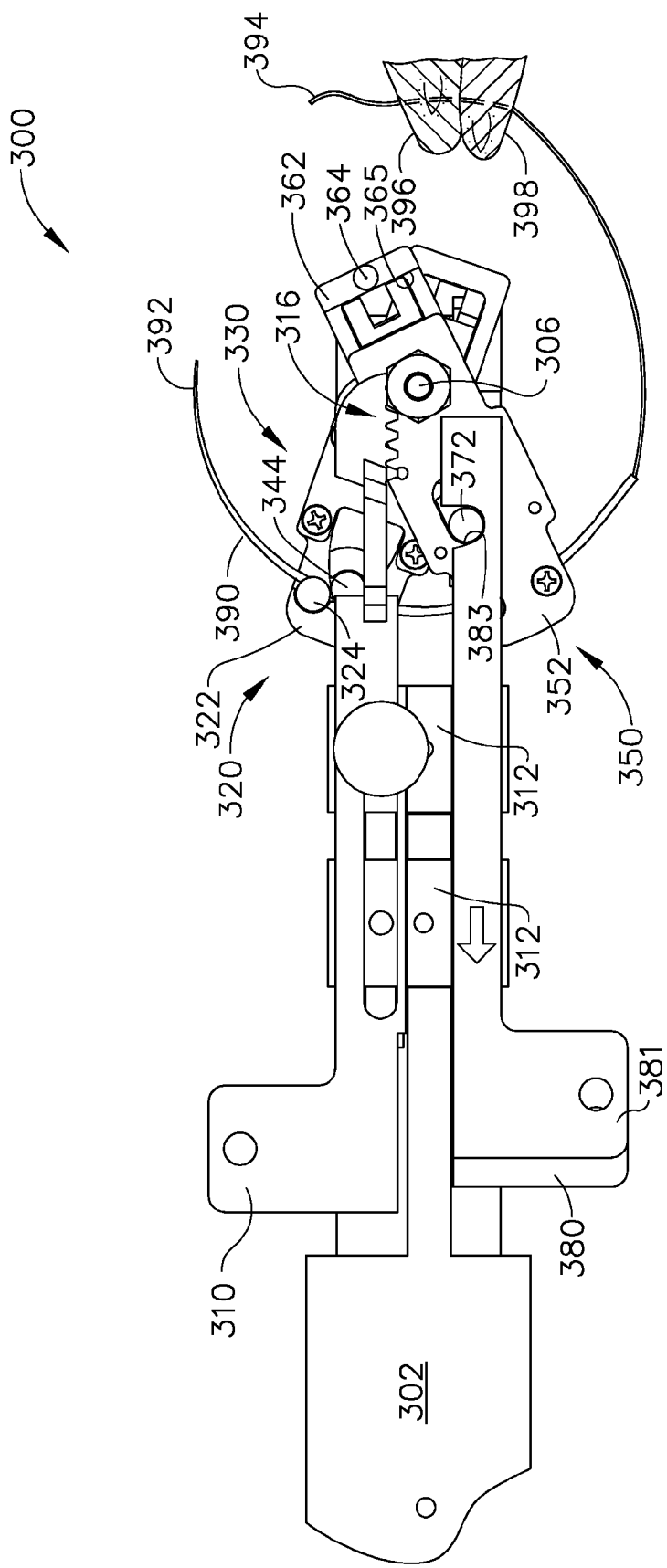
FIG. 26 depicts a partial, cross-sectional side view of the end effector of FIG. 16, in a seventh operational configuration.

Next, actuator (381) is translated proximally as shown in FIG. 26. With cam peg (372) positioned in lateral notch (383), this proximal movement of actuator (381) causes gripping member (370) to slide relative to frame members (352, 360). This sliding of gripping member (370) brings peg (374) closer to pegs (354), such that pegs (354, 374) cooperate to grip needle (390). In addition, this sliding of gripping member (370) causes engagement surfaces (377) of gripping member (370) to move into engagement with engagement surface (365) of second frame member (360). This relationship between engagement surfaces (365, 377) holds gripping member (370) in the position relative to frame members (352, 362) where flex portion (378) is compressed to provide a resilient bias to needle gripping peg (374). Thus, needle (390) remains held by pegs (354, 374) until engagement surfaces (377) are released from engagement with engagement surface (365), as described above, during a subsequent cycle of arms (320, 350).

With arm (350) now gripping needle (390) as described above, actuator (380) is translated distally as shown in FIGS. 27-28, to release needle (390) from arm (320). In particular, chamfered distal end portion (382) pushes against deflection peg (334). This pushing against deflection peg (334) deforms frame member (330) to a point where engagement surface (347) clears engagement surface (335) as shown in FIG. 27. Once engagement surface (347) clears engagement surface (335), the resilient bias of flex portion (348) causes gripping member (340) to extend in length. This extension in length helps cause gripping member (340) to slide relative to frame members (322, 330). In addition, angled surface (332) of frame member (330) interacts with angled surface (346) of gripping member (340) to further cause gripping member (340) to slide relative to frame members (322). With gripping member (340) being slid to the position shown in FIG. 28, peg (344) has substantially separated from pegs (324), such that arm (320) has released needle (390).

In the present example, arm (320) does not release needle (390) until arm (350) has grasped needle (390). In other words, actuator (381) is translated proximally first, then actuator (380) is translated distally in the stages shown in FIGS. 26-27. In some other versions, arm (320) releases needle (390) simultaneously as arm (350) grasps needle (390), such that actuators (380, 381) are translated simultaneously.

It should be understood that in the stage shown in FIG. 28, arm (350) is gripping needle (390) and is positioned at the same angular position shown in FIG. 20. If the user wishes to make an additional pass through layers (396, 398) of tissue to create an additional stitch, the user may simply advance actuator (308) distally to rotate arm (320) back to the position shown in FIG. 20, then move end effector (300) relative to layers (396, 398) of tissue to the desired position. The user may then repeat the above process to repeatedly pass needle (390) and suture (394) through layers (396, 398) of tissue until the desired number of stitches have been placed at the surgical site. The free end of suture (394) may then be knotted, clipped, or otherwise secured. In this example, arm (350) serves a dedicated role as the throwing arm each time needle (390) passes through layers (396, 398) of tissue; while arm (320) serves a dedicated role as the catching arm each time needle (390) passes through layers (396, 398) of tissue. It should be understood that needle (390) rotates in just one forward direction as needle (390) is passed from arm (320) to arm (350) and back to arm (320), such that arms (320, 350) provide a "forward reset" action as referred to above. In other words, while arms (320, 350) do not move through full revolutions in this example, needle (390) does move through full revolutions in this example. It should be understood that end effector (300) may alternatively be used to move needle (390) in a "reverse reset" action as referred to above, if desired. Other suitable ways in which end effector (300) may be used with various kinds of needles will be apparent to those of ordinary skill in the art in view of the teachings herein. Similarly, various other suitable modifications for end effector (300) will be apparent to those of ordinary skill in the art in view of the teachings herein. By way of example only, arms (320, 350) may alternatively selectively grip needle (390) in accordance with any other suitable teachings of U.S. Provisional Application Ser. No. 61/355,832, the disclosure of which is incorporated by reference herein.

In some versions, actuators (308, 310) are together driven by pivoting grip (24) while actuators (380, 381) are driven by button (26). Alternatively, actuators (308, 310) may be associated with their own respective pivoting grips (24) and/or actuators (380, 381) may be associated with their own respective buttons (26). It should also be understood that one or more pivoting grips (24) may actuate arms (320, 350) through the full range of motion depicted in the transition from FIG. 20 to FIG. 28 with just a single act of squeezing pivoting grip (24) toward fixed grip (22). In some such versions, handle portion (20) may provide audible feedback and/or tactile feedback to the user to indicate that arms (320, 350) have reached any one or more of the stages shown in FIGS. 20-28. In some other versions, pivoting grip (24) must be fully actuated once to transition arms (320, 350) from one of the configurations shown in FIGS. 20-28 to another one of the configurations shown in FIGS. 20-28, then be released, then be fully actuated again to transition arms (320, 350) from that other configuration shown in FIGS. 20-28 to yet another one of the configurations shown in FIGS. 20-28. Various suitable components, features, and configurations that may be used to provide such multi-stroke actuation will be apparent to those of ordinary skill in the art in view of the teachings herein. Similarly, various other suitable ways in which arms (320, 350) may be actuated will be apparent to those of ordinary skill in the art in view of the teachings herein.

B. Exemplary Drive Assembly with Rotating Arms and Forward Needle Reset

FIGS. 29-36 depict yet another exemplary end effector (400) that may be incorporated into instrument (10) as an alternative to end effector (40) described above. It should also be understood that end effector (400) may be incorporated into various other instruments, such that end effector (400) is not limited to instrument (10). End effector (400) of this example is disposed at the distal end of a shaft (402) and includes a pair of arms (420, 450) that selectively throw and catch a needle (490). Each arm (420, 450) is secured to a respective axle (404) (only one axle (404) is shown in FIGS. 29-36), and each arm (420, 450) rotates about its respective axle (404) as will be described in greater detail below. While axles (404) are aligned along a common axis, axles (404) are separate from each other such that a gap is defined between axles (404), with that gap also lying along the common axis. Axles (304) are pivotally secured to shaft (402). The axis along which axles (404) are aligned and oscillate is perpendicular to a longitudinal axis defined by shaft (402). Thus, arms (420, 450) oscillate along respective planes that are parallel to the longitudinal axis defined by shaft (402) and that are parallel to each other. In the present example, arms (420, 450) also move asynchronously, such that one arm (420, 450) may remain stationary as the other arm (450, 420) is moving.

Arms (420, 450) of the present example are substantially identical to arms (320, 350) described above. Therefore, the following description will simply discuss the differences between arms (420, 450) and arms (320, 350). It may be assumed that the remaining details of arms (420, 450) are the same as the remaining details of arms (320, 350). Of course, arms (420, 450) may alternatively have various other differences with arms (320, 350), if desired. One notable difference between arms (420, 450) of the present example and arms (320, 350) described above is that a pulley (not shown) is coaxially disposed about each axle (404), in the same location where pinion portion (305) is located in arms (320, 350). In addition, a continuous loop cable, belt, or chain (not shown) is wrapped around each pulley, such that pulling/pushing on each cable, belt, or chain will cause the corresponding arm (420, 450) to rotate. In other words, longitudinal movement of each cable, belt, or chain provides corresponding rotation of the associated pulley. Since each pulley is unitary with a respective arm (420, 450) via the corresponding axle (404), the rotational motion of each pulley provides corresponding rotation of the respective arm (420, 450). It should therefore be understood that such a cable, belt, or chain may be viewed as a substitute for arm rotation actuators (308, 310) and rack portions (314, 316) from end effector (300). Another notable difference between arms (420, 450) of the present example and arms (320, 350) described above is that arms (420, 450) rotate through full revolutions during operation of end effector (400) in this example as will be described in greater detail below; whereas arms (320, 350) merely rock or oscillate during operation of end effector (300) as described above. Of course, end effector (400) may alternatively be operated in a manner whereby arms (420, 450) merely rock, oscillate, or otherwise fail to complete full revolutions during operation of end effector (400).

It should also be understood that the cables, belts, or chains that provide rotation of arms (420, 450) may be driven in numerous different ways. By way of example only, the cables, belts, or chains may be manually driven by one or more knobs or other features. As another merely illustrative example, the cables, belts, or chains may be driven by one or more motors. Other suitable components and features that may be used to drive the cables, belts, or chains will be apparent to those of ordinary skill in the art in view of the teachings herein. Similarly, other suitable components and features that may be used in lieu of or in addition to cables, belts, or chains will be apparent to those of ordinary skill in the art. By way of example only, each axle (404) may include an integral bevel gear that is driven by a complementary bevel gear disposed at the distal end of a rotatable drive shaft that is disposed within shaft (402).

Needle (490) of this example includes a sharp tip (492) at one end and a suture (494) secured to the other end. Alternatively, both ends of needle (490) may include sharp tips, with suture (494) being secured in a middle region of needle (490) between the sharp tips. While needle (490) is curved in this example, some other versions may include use of a straight needle, an angled needle, or any other suitable type of needle.

Figure 29:
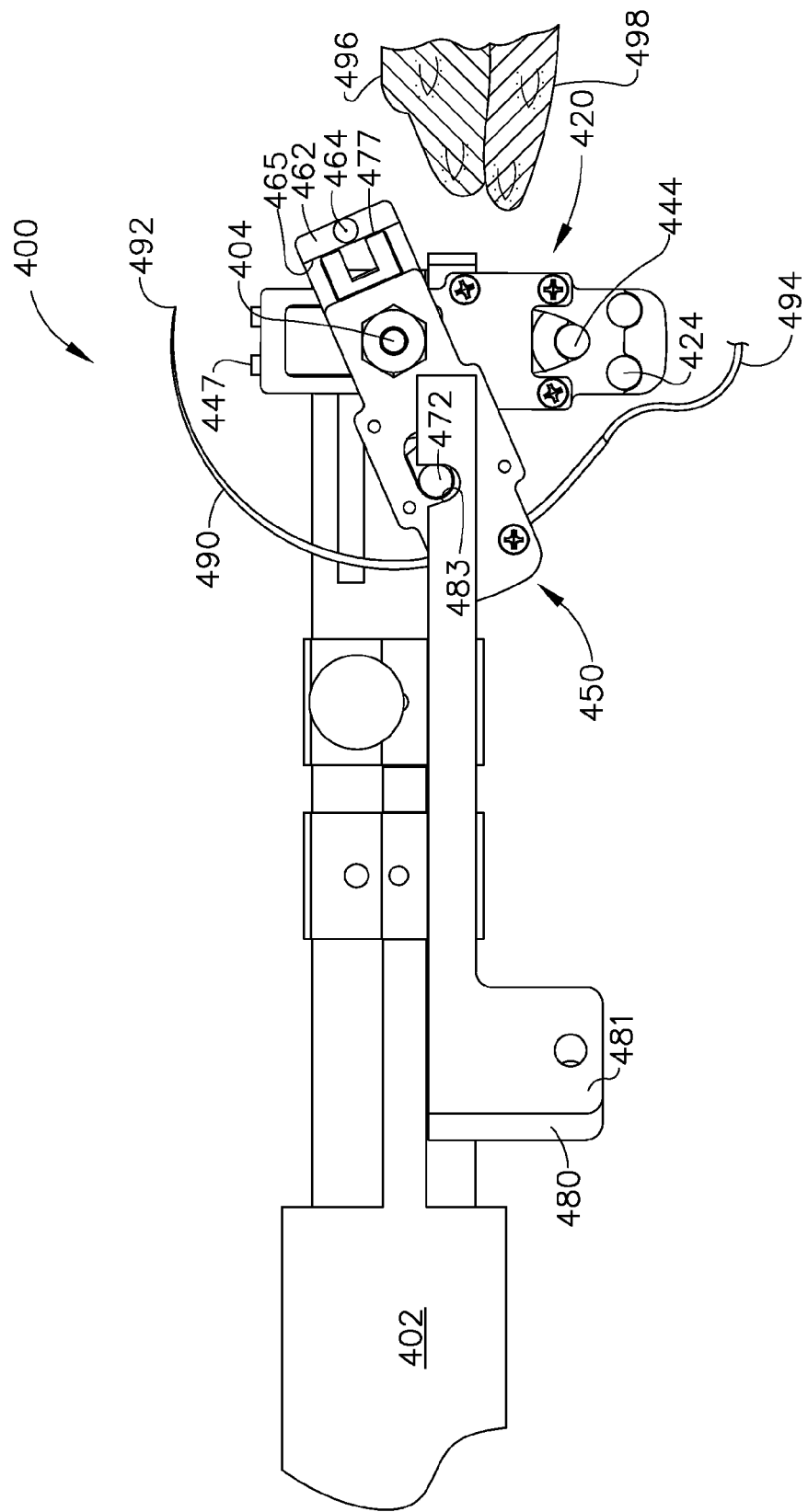
FIG. 29 depicts a partial, cross-sectional side view of an exemplary alternative end effector for a laparoscopic suturing device, in a first operational configuration.

In an exemplary method of operation, end effector (400) is positioned near two layers (496, 498) of tissue, as shown in FIG. 29. At this stage, needle (490) is gripped by pegs (not shown) of arm (450). In particular, a needle gripping member of arm (450) is positioned such that engagement surfaces (477) of the gripping member are engaged with an engagement surface (465) of a second frame member of arm (450). This relationship holds the gripping member in a position relative to frame members of arm (450) whereby a flex portion of the needle gripping member is compressed and provides a resilient bias to a needle gripping peg, such that needle (490) remains held by pegs of arm (450) until the gripping member is slid relative to the frame members of arm (450) during subsequent operation of end effector (400) as will be described in greater detail below.

Figure 30:
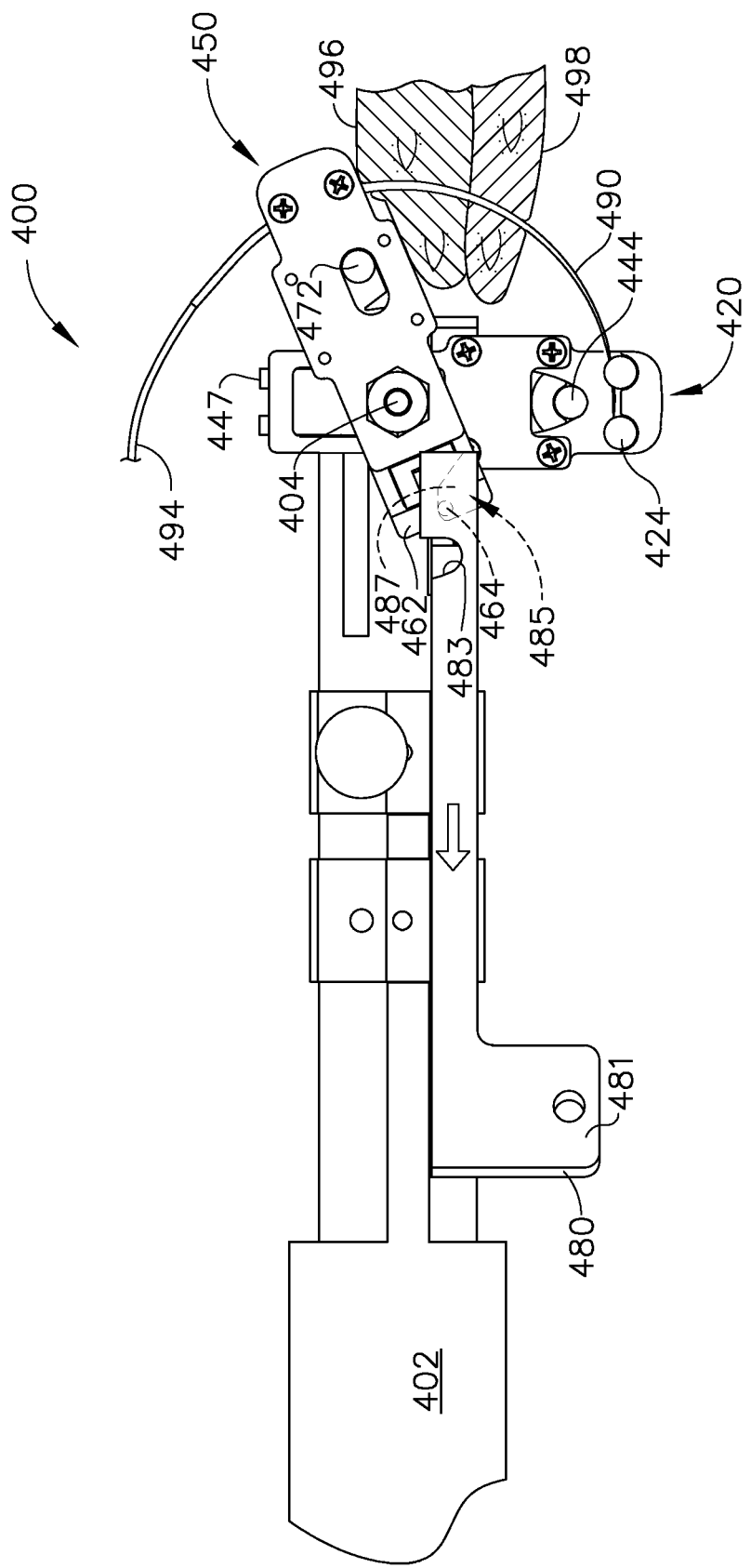
FIG. 30 depicts a partial, cross-sectional side view of the end effector of FIG. 29, in a second operational configuration.

With end effector (400) positioned near layers (496, 498) of tissue, and with needle (490) being held by pegs of arm (450), the user may actuate a cable, belt, or chain to rotate arm (450) forward as shown in FIG. 30. The forward rotation of arm (450) causes sharp tip (492) of needle (490) to pierce and penetrate both layers (496, 498) of tissue. As also shown in FIG. 30, actuator (481) is translated proximally, positioning a recess (485) of actuator (481) to receive deflection peg (464) of arm (450). A proximal surface in recess (485) helps arrest further distal rotation of arm (450) by engaging peg (464). Arm (420) remains substantially stationary at this stage. Needle gripping pegs (424, 444) of arm (420) are positioned apart at this stage, such that arm (420) may freely receive needle (490). In some versions, arm (420) may be rotated to engage lower layer (498) of tissue to assist in clamping or providing ground against the tissue as needle (490) is inserted through layers (496, 498) of tissue at this stage. For instance, arm (420) may be rotated to the position shown in FIG. 31 as described in greater detail below, before arm (450) is rotated to the position shown in FIG. 30 as described above.

Figure 31:
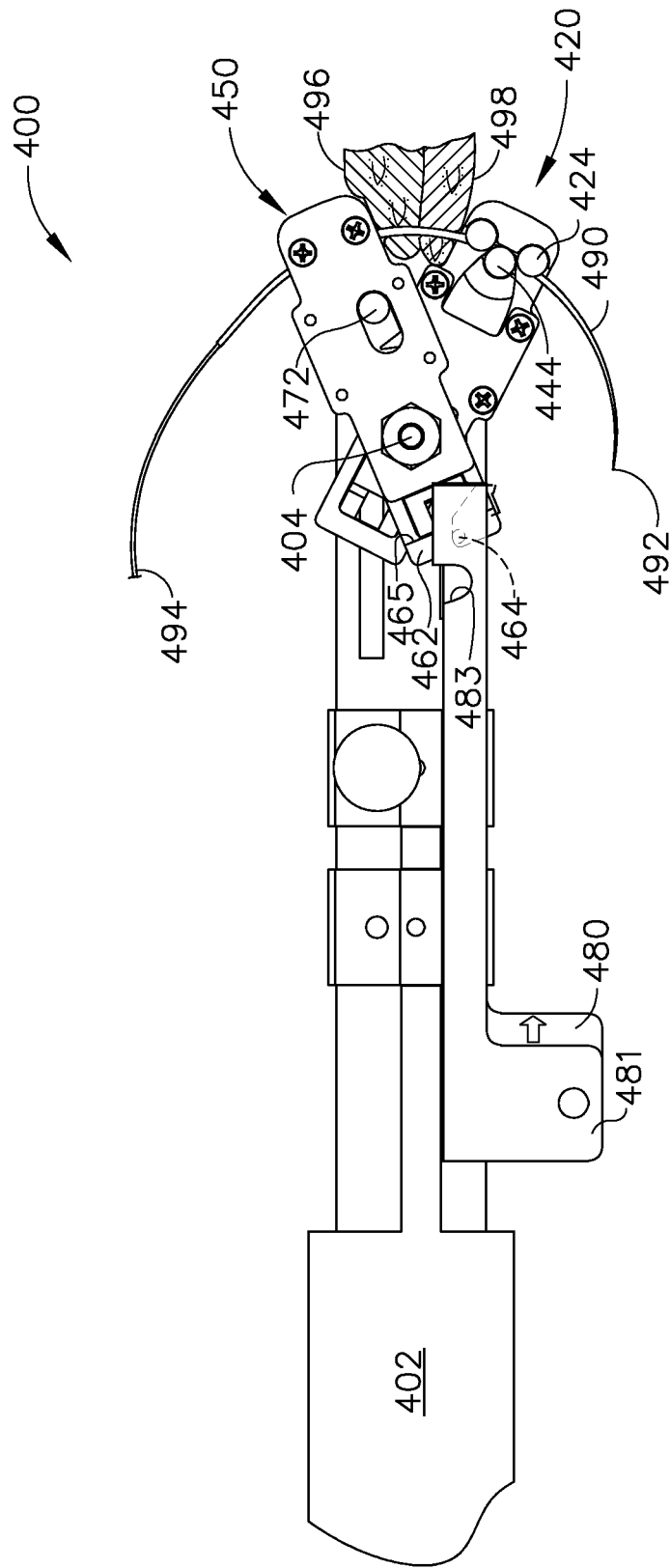
FIG. 31 depicts a partial, cross-sectional side view of the end effector of FIG. 29, in a third operational configuration.

With needle (490) disposed in layers (496, 498) of tissue, and with needle (490) still being held by pegs of arm (450), the user may actuate a cable, belt, or chain to rotate arm (420) as shown in FIG. 31. Arm (420) is engaged against lower layer (498) of tissue, such that both layers (496, 498) of tissue are compressed between arms (420, 450) at this stage. In addition, needle gripping pegs (424, 444) of arm (320) are actuated to grip needle (490). In particular, actuator (480) of translated distally. This drives a distal end portion of actuator (480) into a cam peg of arm (420). Such pushing of the cam peg slides a needle gripping member of arm (420) relative to frame members of arm (420), bringing needle gripping peg (444) closer to needle gripping pegs (424) such that needle (490) is received in notches of pegs (424, 444). In addition, this sliding of the needle gripping member causes engagement surface (447) to snap into place in contact with an engagement surface of a frame member of arm (420). With these engagement surfaces in contact with each other, the needle gripping member is held in the position shown in FIG. 31. In this position, a flex portion of the needle gripping member of arm (420) is compressed, providing a resilient bias to needle gripping peg (444). This resilient bias helps to keep needle (490) gripped by pegs (424, 444) until the gripping member of arm (420) is slid relative to the frame members of arm (420) during subsequent operation of end effector (400) as will be described in greater detail below.

Figure 32:
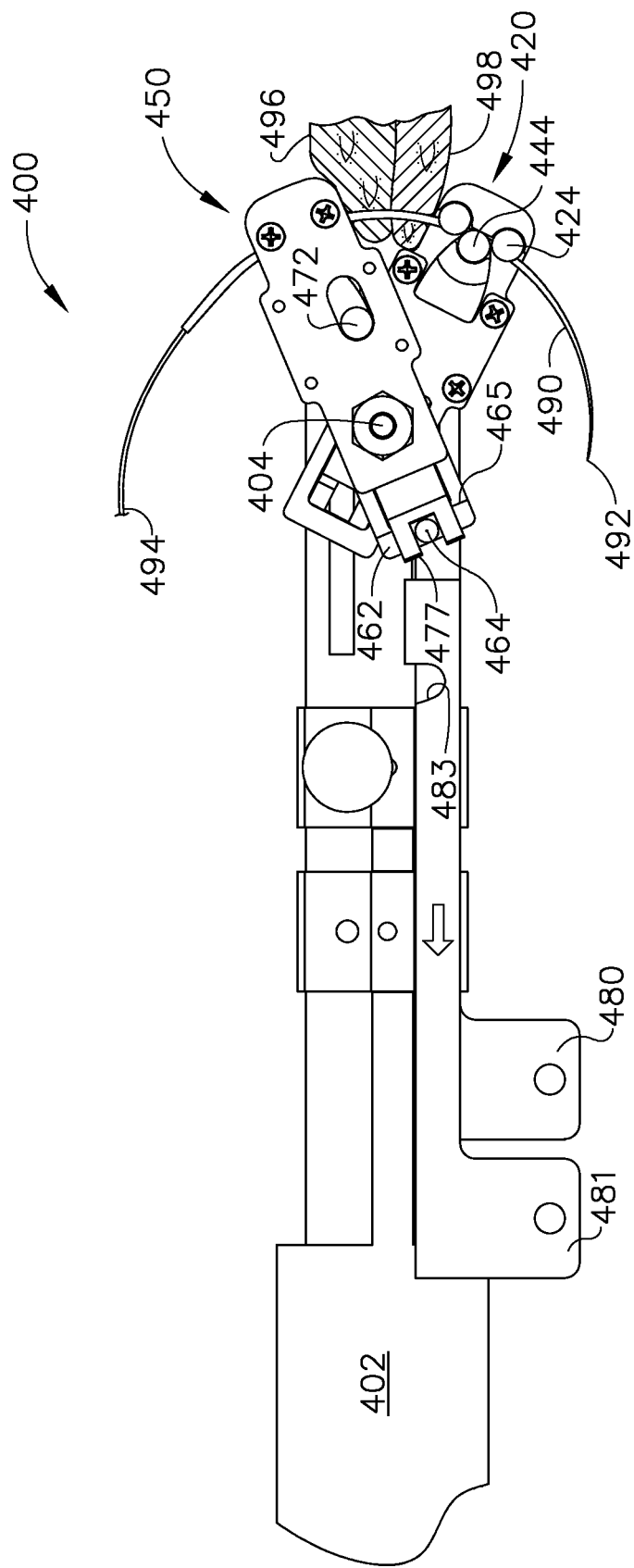
FIG. 32 depicts a partial, cross-sectional side view of the end effector of FIG. 29, in a fourth operational configuration.

With arm (420) gripping needle (490), actuator (481) is translated proximally to release needle (490) from arm (450) as shown in FIG. 32. In particular, when actuator (481) is translated proximally with arm (450) in the rotational position shown in FIGS. 30-31, angled lateral surface (487) of distal recess (485) pushes against deflection peg (464). This pushing against deflection peg (464) deforms a frame member of arm (450) to a point where engagement surface (477) clears engagement surface (465). Once engagement surface (477) clears engagement surface (465), the resilient bias of the flex portion of arm (450) causes the gripping member of arm (450) to extend in length. This extension in length helps cause the gripping member of arm (450) to slide relative to the frame members of arm (450). In addition, an angled surface of one of the frame member of arm (450) interacts with an angled surface of the gripping member of arm (450) to further cause the gripping member of arm (450) to slide relative to the frame members of arm (450). With the gripping member of arm (450) being slid to the position shown in FIG. 32, needle gripping pegs of arm (450) have substantially separated, such that arm (450) has released needle (490).

In the present example, arm (450) does not release needle (490) until arm (420) has grasped needle (490). In other words, actuator (480) is translated distally first, then actuator (481) is translated proximally in the stages shown in FIGS. 31-32. In some other versions, arm (450) releases needle (490) simultaneously as arm (420) grasps needle (490), such that actuators (480, 481) are translated simultaneously.

Figure 33:
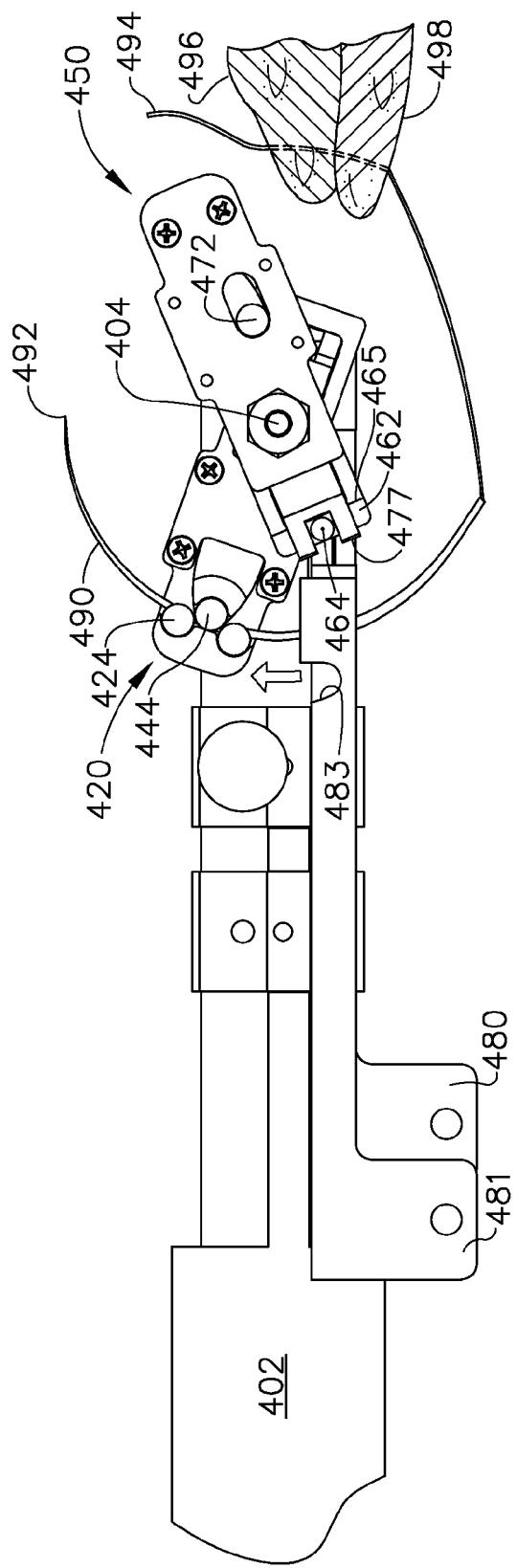
FIG. 33 depicts a partial, cross-sectional side view of the end effector of FIG. 29, in a fifth operational configuration.

With arm (420) having grasped needle (490) and with arm (450) having released needle (490), arm (422) is further rotated proximally to pull needle (490) free of layers (496, 498) of tissue and to pull suture (494) through layers (496, 498) of tissue as shown in FIG. 33. This is accomplished by actuating the cable, belt, or chain that rotatably drives arm (420). Arm (450) remains substantially stationary at this stage.

Figure 34:
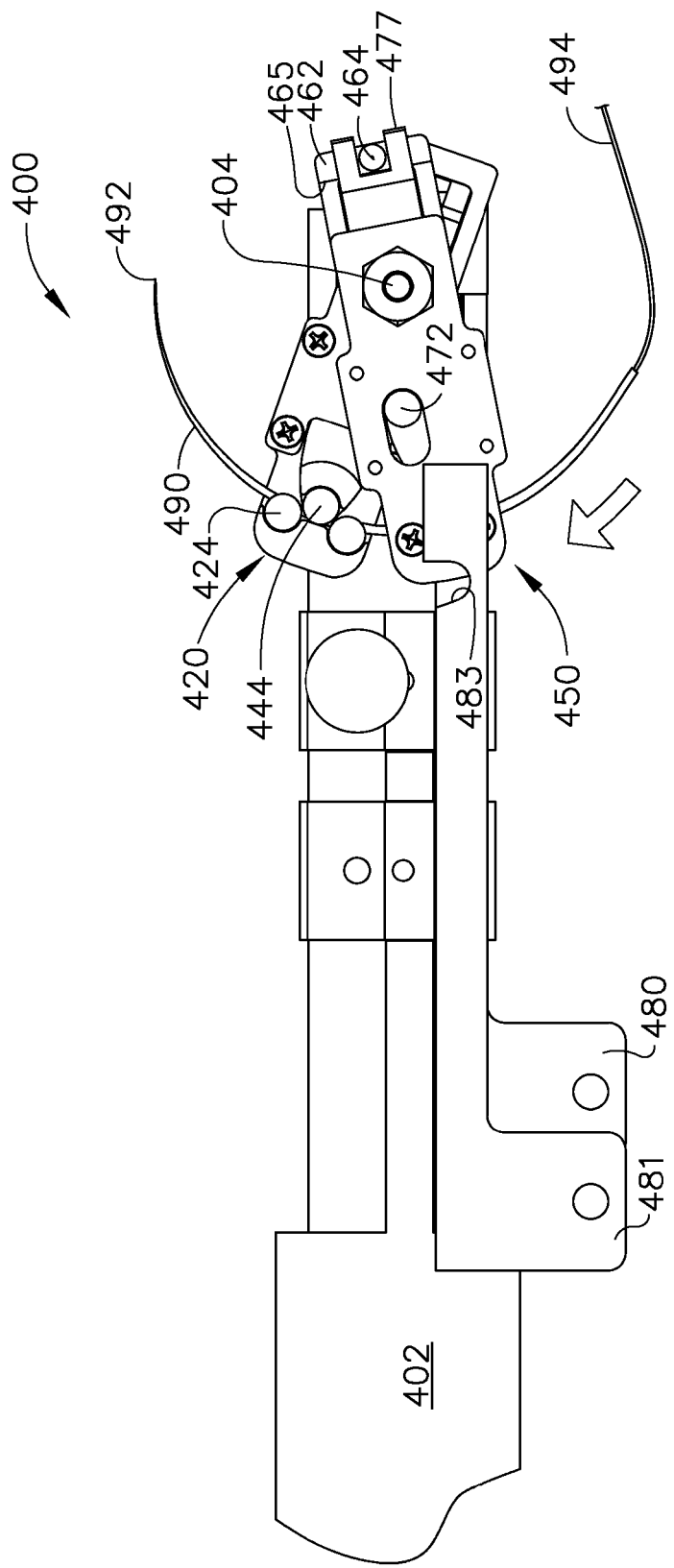
FIG. 34 depicts a partial, cross-sectional side view of the end effector of FIG. 29, in a sixth operational configuration.

As shown in FIG. 34, end effector (400) is then moved away from layers (496, 498) of tissue to tension suture (494); and arms (420, 450) are rotatably positioned to transfer needle (490) from arm (420) back to arm (450). In particular, a cable, belt, or chain associated with arm (450) is actuated to rotate arm (450) to the position shown in FIG. 34. At this stage, needle gripping pegs (424, 444) of arm (420) continue to grip needle (490); while needle gripping pegs of arm (450) are positioned apart to freely receive needle (490).

Figure 35:
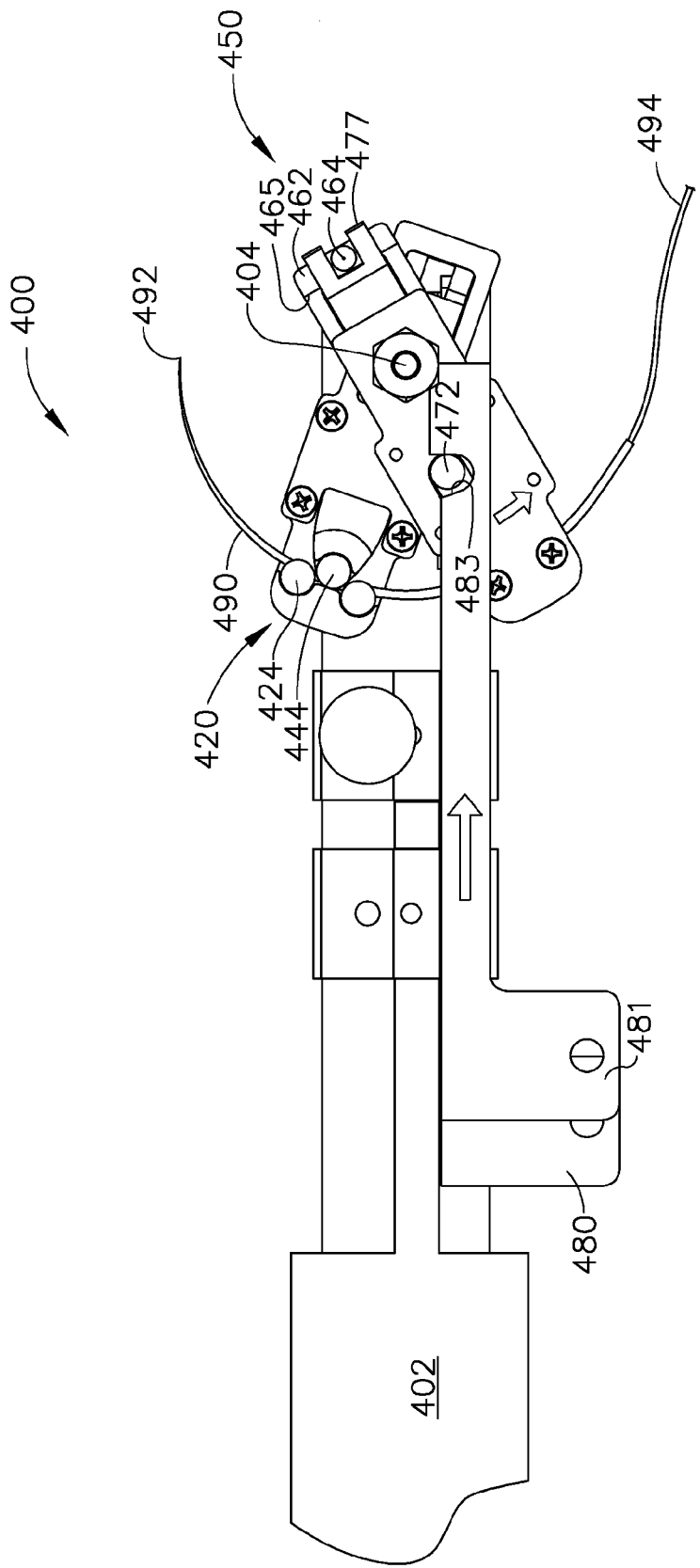
FIG. 35 depicts a partial, cross-sectional side view of the end effector of FIG. 29, in a seventh operational configuration.
Figure 36:
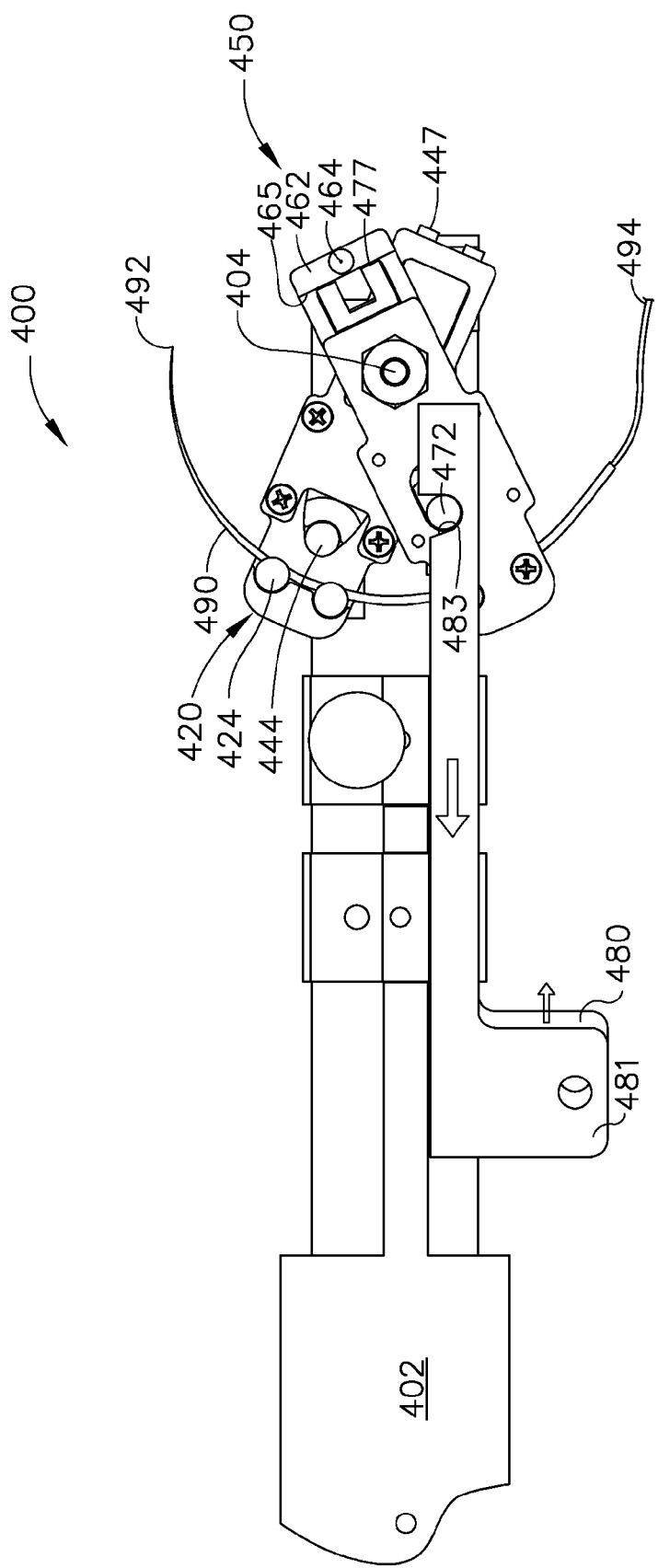
FIG. 36 depicts a partial, cross-sectional side view of the end effector of FIG. 29, in an eighth operational configuration.

Next, actuator (381) is translated distally and then arm (450) is rotated back distally, as shown in FIG. 35. These motions position cam peg (472) in lateral notch (483) of actuator (481). Arm (420) remains stationary at this stage, and continues to grip needle (420). To transfer control of needle (490) from arm (420) back to arm (450), actuator (481) is translated proximally and actuator (480) is translated distally, as shown in FIG. 36. With cam peg (472) in lateral notch (483), this proximal movement of arm (481) causes the gripping member of arm (450) to slide relative to the frame members of arm (450), which brings needle gripping pegs of arm (450) closer together to grip needle (490). In addition, the sliding of the gripping member of arm (450) causes engagement surfaces (477) to move into engagement with engagement surface (465), thereby holding the gripping member of arm (450) in a position where a flex portion is compressed to provide a resilient bias to one of the needle gripping pegs. Thus, needle (490) will remain held by the needle gripping pegs of arm (450) until engagement surfaces (477) are released from engagement with engagement surface (465), as described above, during a subsequent cycle of arms (420, 450).

As is also shown in FIG. 36 and as noted above, actuator (480) is translated distally at this stage in order to release needle (490) from arm (420). Due to a camming engagement between part of actuator (480) and arm (420), this distal movement of actuator causes arm (420) to release needle (490) in a manner similar to that described above with reference to FIGS. 27-28. In the present example, arm (420) releases needle (490) at substantially the same time that arm (450) grasps needle. In some other versions, arm (420) does not release needle (490) until arm (450) has grasped needle (490).

It should be understood that in the stage shown in FIG. 36, arm (450) is gripping needle (490) and is positioned at the same angular position shown in FIG. 29. If the user wishes to make an additional pass through layers (496, 498) of tissue to create an additional stitch, the user may actuate the cable, belt, or chain associated with arm (420) to rotate arm (420) back to the position shown in FIG. 29 (e.g., in a clockwise direction in the view shown in FIGS. 29-36), then move end effector (400) relative to layers (496, 498) of tissue to the desired position. The user may then repeat the above process to repeatedly pass needle (490) and suture (494) through layers (496, 498) of tissue until the desired number of stitches have been placed at the surgical site. The free end of suture (494) may then be knotted, clipped, or otherwise secured. In this example, arm (450) serves a dedicated role as the throwing arm each time needle (490) passes through layers (496, 498) of tissue; while arm (420) serves a dedicated role as the catching arm each time needle (490) passes through layers (496, 498) of tissue. It should be understood that needle (490) rotates in just one forward direction as needle (490) is passed from arm (420) to arm (450) and back to arm (420), such that arms (420, 450) provide a "forward reset" action as referred to above. In other words, needle (490) moves through full revolutions in this example. Other suitable ways in which end effector (400) may be used with various kinds of needles will be apparent to those of ordinary skill in the art in view of the teachings herein. Similarly, various other suitable modifications for end effector (400) will be apparent to those of ordinary skill in the art in view of the teachings herein. By way of example only, arms (420, 450) may alternatively selectively grip needle (490) in accordance with any other suitable teachings of U.S. Provisional Application Ser. No. 61/355,832, the disclosure of which is incorporated by reference herein.

In some versions, the cables, belts, chains, bevel gears, etc. that respectively rotate arms (420, 450) are together driven by pivoting grip (24) while actuators (480, 481) are driven by button (26). Alternatively, the cables, belts, chains, bevel gears, etc. that respectively rotate arms (420, 450) may be associated with their own respective pivoting grips (24) and/or actuators (480, 481) may be associated with their own respective buttons (26). It should also be understood that one or more pivoting grips (24) may actuate arms (420, 450) through the full range of motion depicted in the transition from FIG. 29 to FIG. 36 with just a single act of squeezing pivoting grip (24) toward fixed grip (22). In some such versions, handle portion (20) may provide audible feedback and/or tactile feedback to the user to indicate that arms (420, 450) have reached any one or more of the stages shown in FIGS. 29-36. In some other versions, pivoting grip (24) must be fully actuated once to transition arms (420, 450) from one of the configurations shown in FIGS. 29-36 to another one of the configurations shown in FIGS. 29-36, then be released, then be fully actuated again to transition arms (420, 450) from that other configuration shown in FIGS. 29-36 to yet another one of the configurations shown in FIGS. 29-36. Various suitable components, features, and configurations that may be used to provide such multi-stroke actuation will be apparent to those of ordinary skill in the art in view of the teachings herein. Similarly, various other suitable ways in which arms (420, 450) may be actuated will be apparent to those of ordinary skill in the art in view of the teachings herein.

IV. EXEMPLARY SUTURE DEVICE WITH DRIVE ASSEMBLY HAVING VIRTUAL PIVOT

FIGS. 37-41 depict still another exemplary end effector (500) that may be incorporated into instrument (10) as an alternative to end effector (40) described above. It should also be understood that end effector (500) may be incorporated into various other instruments, such that end effector (500) is not limited to instrument (10). End effector (500) of this example is disposed at the distal end of a shaft (502) and includes a pair of arms (520, 550) that selectively throw and catch a needle (590). As will be described in greater detail below, arms (520, 550) move in an asynchronous fashion in the present example. In addition, needle (590) rotates in just one forward direction as needle (590) is passed from arm (520) to arm (550) and back to arm (520), such that arms (520, 550) provide a "forward reset" action as referred to above. In other words, needle (590) moves through full revolutions in this example.

Needle (590) of this example includes a sharp tip (592) at one end and a suture (594) secured to the other end. Alternatively, both ends of needle (590) may include sharp tips, with suture (594) being secured in a middle region of needle (590) between the sharp tips. While needle (590) is curved in this example, some other versions may include use of a straight needle, an angled needle, or any other suitable type of needle.

Arm (520) of the present example includes a needle gripping feature (522). Needle gripping feature (522) may be configured and operable in accordance with at least some of the teachings of U.S. Provisional Application Ser. No. 61/355,832, the disclosure of which is incorporated by reference herein. Alternatively, needle gripping feature (522) may have any other suitable components, features, configurations, or operability, etc. Arm (520) is driven by an actuator (524), which reciprocates within shaft (502) in the present example. A link (530) provides a pivotal coupling between arm (520) and actuator (524). In particular, link (530) is pivotally coupled with arm (520) by a pivot pin (532); while link (530) is pivotally coupled with actuator (524) by a pivot pin (534). In addition, a pin (540) is disposed through a middle region of arm (520), such that arm (520) is pivotable about pin (540). Of course, pins (532, 534, 540) may comprise rivets, screws, and/or any other structural features that allow pivoting.

While pin (540) is in the middle region of arm (520) in this example, pin (540) is not centered along the length of arm (520). It should be understood that pin (540) may be located at any suitable position along the length of arm (520). Pin (540) is slidably disposed in a slot (504) that is formed in an integral portion of shaft (502). Thus, pin (540) may reciprocate relative to shaft (502), along slot (504). As can be seen from viewing FIGS. 37-40 in a series, pin (540) reciprocates in slot (504) as actuator (524) reciprocates in shaft (502). As can also be seen from viewing FIGS. 37-40 and as will be described in greater detail below, this reciprocation results in needle gripping feature (522) moving along a circular path. Thus, actuator (524), link (530), pivots (532, 534, 540), slot (540), and arm (520) all cooperate such that actuator (524) drives needle gripping feature (522) in a manner similar to that found in a locomotive drive for a steam engine train, etc. While needle gripping feature (522) is moved along a circular path in the present example, in some other versions needle gripping feature (522) may be moved along an ovular path, an elliptical path, an octagonal path, or some other path that is substantially circular. Alternatively, needle gripping feature may move along some other type of path.

Figure 40:
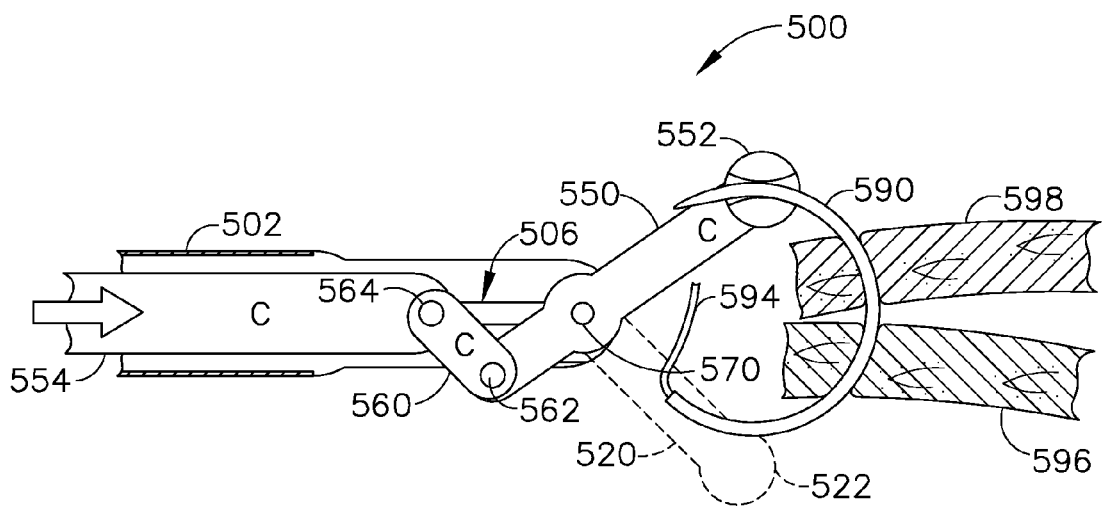
FIG. 40 depicts a partial, cross-sectional side view of the end effector of FIG. 37, in a fourth operational configuration.
Figure 41:
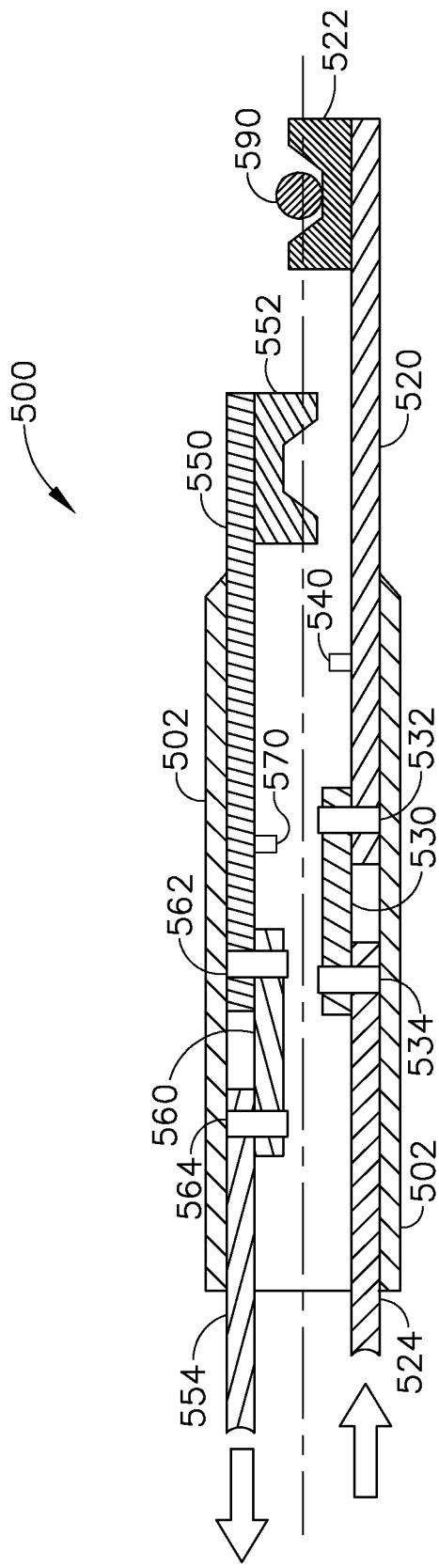
FIG. 41 depicts a partial, cross-sectional top view of the end effector of FIG. 37, in the first operational configuration The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

As best seen in FIGS. 40-41, arm (550) of the present example includes a needle gripping feature (552). Needle gripping feature (552) may be configured and operable in accordance with at least some of the teachings of U.S. Provisional Application Ser. No. 61/355,832, the disclosure of which is incorporated by reference herein. Alternatively, needle gripping feature (552) may have any other suitable components, features, configurations, or operability, etc. Arm (550) is driven by an actuator (554), which reciprocates within shaft (502) in the present example. A link (560) provides a pivotal coupling between arm (550) and actuator (554). In particular, link (560) is pivotally coupled with arm (550) by a pivot pin (562); while link (560) is pivotally coupled with actuator (554) by a pivot pin (564). In addition, a pin (570) is disposed through a middle region of arm (550), such that arm (550) is pivotable about pin (570). Of course, pins (562, 564, 570) may comprise rivets, screws, and/or any other structural features that allow pivoting.

While pin (570) is in the middle region of arm (550) in this example, pin (570) is not centered along the length of arm (550). It should be understood that pin (570) may be located at any suitable position along the length of arm (550). Pin (570) is slidably disposed in a slot (506) that is formed in an integral portion of shaft (502). Thus, pin (570) may reciprocate relative to shaft (502), along slot (506). Pin (570) reciprocates in slot (506) as actuator (554) reciprocates in shaft (502). As will be described in greater detail below, this reciprocation results in needle gripping feature (552) moving along a circular path. Thus, actuator (554), link (560), pins (562, 564, 570), slot (570), and arm (550) all cooperate such that actuator (554) drives needle gripping feature (552) in a manner similar to that found in a locomotive drive for a steam engine train, etc. While needle gripping feature (552) is moved along a circular path in the present example, in some other versions needle gripping feature (552) may be moved along an ovular path, an elliptical path, an octagonal path, or some other path that is substantially circular. Alternatively, needle gripping feature may move along some other type of path.

Figure 37:
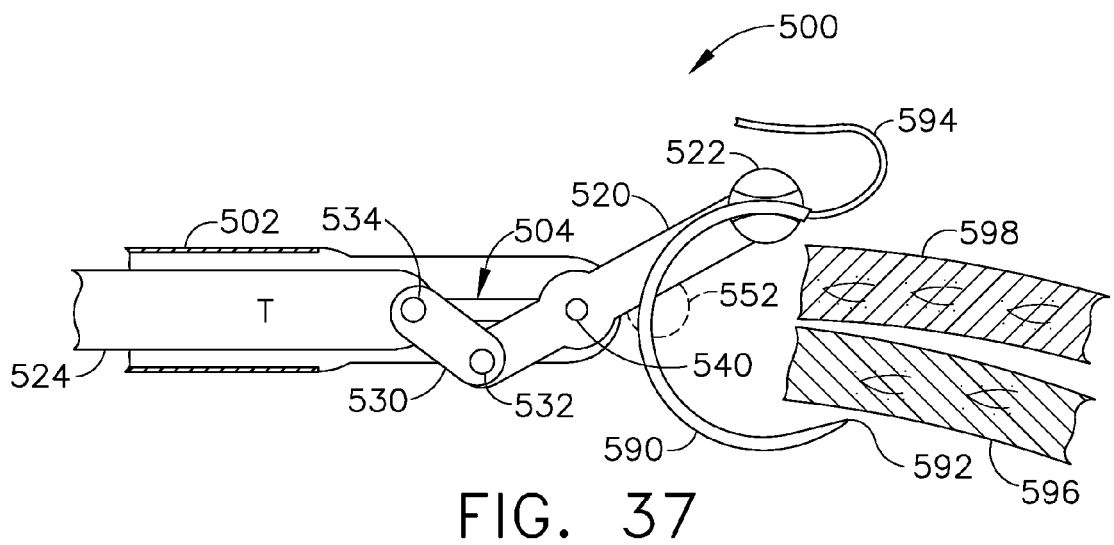
FIG. 37 depicts a partial, cross-sectional side view of another exemplary alternative end effector for a laparoscopic suturing device, in a first operational configuration.
Figure 38:
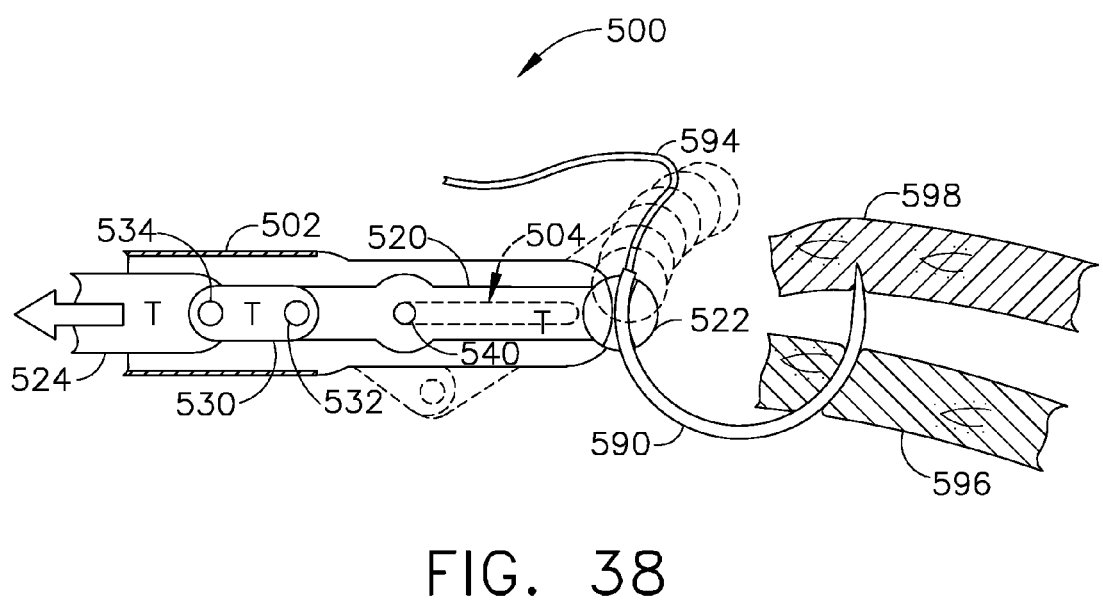
FIG. 38 depicts a partial, cross-sectional side view of the end effector of FIG. 37, in a second operational configuration.

In an exemplary method of operation, end effector (500) is positioned near two layers (596, 598) of tissue, with sharp tip (592) of needle (590) being positioned just below layer (596) as shown in FIG. 37. Then, actuator (524) is retracted proximally to the position shown in FIG. 38. This proximal movement of actuator (524) causes link (530) to pull and pivot arm (520), which in turn rotates needle (590) to drive tip (592) into layers (596, 598) of tissue. Arm (550) remains substantially stationary during this stage since actuator (554) and link (560) are independent from actuator (524) and link (530). As can also be seen in FIG. 38, actuator (524), link (530), arm (520), and pins (532, 534, 540) are all substantially aligned with each other at this stage. Pin (540) has moved from a distal end of slot (504) to a proximal end of slot (504).

Figure 39:
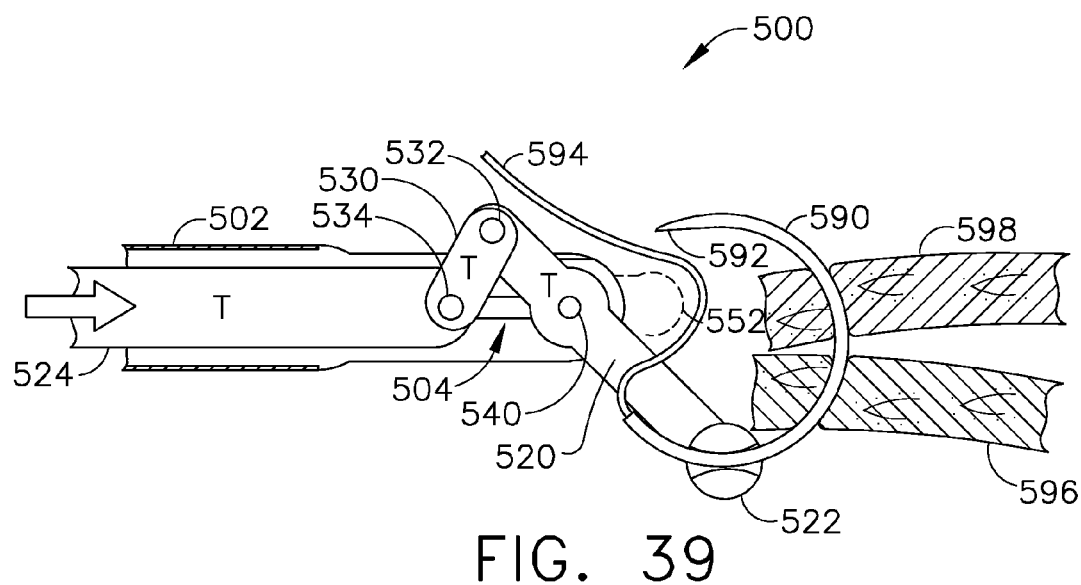
FIG. 39 depicts a partial, cross-sectional side view of the end effector of FIG. 37, in a third operational configuration.

Next, actuator (524) is advanced distally to the position shown in FIG. 39. This distal movement of actuator (524) causes link (530) to push and pivot arm (520), which in turn continues to rotate needle (590) in the same direction as previously, to drive needle (590) further through layers (596, 598) of tissue. It should be noted that needle (590) has moved through an angular range of approximately 180° along a circular path in the transition from the position shown in FIG. 37 to the position shown in FIG. 39. With needle (590) so positioned, actuator (554) is advanced distally to the position shown in FIG. 40. This distal movement of actuator (524) causes link (560) to push and pivot arm (550), which in turn positions needle gripping feature (552) about needle (590). Arm (520) remains substantially stationary at this stage. With arm (550) being positioned as shown in FIG. 40, arm needle gripping feature (552) grasps needle (590) and needle gripping feature (522) releases needle (590). In some versions, needle gripping feature (522) does not release needle (590) until needle gripping feature (552) has grasped needle (590). In some other versions, needle gripping feature (522) releases needle (590) simultaneously as needle gripping feature (552) grasps needle (590).

With needle gripping feature (552) grasping needle (590) and with needle gripping feature (522) having released needle (590), actuator (554) is then retracted proximally to cause link (560) to pull and pivot arm (550), which in turn rotates needle (590) further along a circular path to pull needle (590) free of layers (596, 598) and to pull suture (594) through layers (596, 598). For instance, at this stage (not depicted) actuator (554), link (560), arm (550), and pins (562, 564, 570) may be substantially aligned with each other, with pin (570) being positioned at the proximal end of slot (506). Actuator (554) may then be advanced distally to cause link (560) to push and pivot arm (550), which in turn continues to rotate needle (590) further along a circular path to a position similar to that shown in FIG. 37. The user may then pull end effector (500) further away from layers (596, 598) to tension suture (594), and may then re-position end effector (500) to perform another stitch. At this stage (or before end effector (500) is moved and/or re-positioned), actuator (524) may be reciprocated to locate needle gripping feature (522) at the position shown in FIG. 37; and to transfer control of needle (590) from arm (550) back to arm (520). Once control of needle (590) has been transferred from arm (550) back to arm (520), actuator (554) may be retracted proximally to locate needle gripping feature (552) at the position shown in FIG. 37. The user may then repeat the above process to repeatedly pass needle (590) and suture (594) through layers (596, 598) of tissue until the desired number of stitches have been placed at the surgical site. The free end of suture (594) may then be knotted, clipped, or otherwise secured. In this example, arm (520) serves a dedicated role as the throwing arm each time needle (590) passes through layers (596, 598) of tissue; while arm (550) serves a dedicated role as the catching arm each time needle (590) passes through layers (596, 598) of tissue. Other suitable ways in which end effector (500) may be used with various kinds of needles will be apparent to those of ordinary skill in the art in view of the teachings herein.

Actuators (524, 554) extend along the length of shaft (502) and are selectively translated by one or more features at handle portion (20) in the present example. For instance, each actuator (524, 554) may be associated with a respective pivoting grip (24) via rack and pinion configurations, camming features, etc. Alternatively, actuators (524, 554) may be operated by sliders, motors, solenoids, or any other suitable driving components as will be apparent to those of ordinary skill in the art in view of the teachings herein. It should also be understood that actuators (524, 554) are operable independently relative to each other in the present example. Actuators (524, 554) may be associated with their own respective pivoting grips (24) and/or needle gripping features (522, 552) may be associated with their own respective buttons (26). It should also be understood that one or more pivoting grips (24) may actuate arms (520, 550) through the full range of motion depicted in the transition from FIG. 37 to FIG. 40 with just a single act of squeezing pivoting grip (24) toward fixed grip (22). In some such versions, handle portion (20) may provide audible feedback and/or tactile feedback to the user to indicate that arms (520, 550) have reached any one or more of the stages shown in FIGS. 37-40. In some other versions, pivoting grip (24) must be fully actuated once to transition arms (520, 550) from one of the configurations shown in FIGS. 37-40 to another one of the configurations shown in FIGS. 37-40, then be released, then be fully actuated again to transition arms (520, 550) from that other configuration shown in FIGS. 37-40 to yet another one of the configurations shown in FIGS. 37-40. Various suitable components, features, and configurations that may be used to provide such multi-stroke actuation will be apparent to those of ordinary skill in the art in view of the teachings herein. Similarly, various other suitable ways in which arms (520, 550) may be actuated will be apparent to those of ordinary skill in the art in view of the teachings herein. Similarly, various other suitable components, features, and configurations for end effector (500) will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
 (a) a shaft, wherein the shaft defines a longitudinal axis; and
 (b) an end effector, wherein the end effector comprises:
  (i) a needle throwing arm, wherein the needle throwing arm is operable to selectively engage a surgical needle, wherein the needle throwing arm is movable along a plane that is substantially parallel to the longitudinal axis of the shaft,
(ii) a needle receiving arm, wherein the needle receiving arm is operable to selectively engage a surgical needle transferred from the needle throwing arm, wherein the needle receiving arm is movable along a plane that is substantially parallel to the longitudinal axis of the shaft,
(iii) a first axle, wherein the needle throwing arm is pivotable about the first axle, and
(iv) a second axle, wherein the needle receiving arm is pivotable about the second axle,
wherein the first axle is separate from the second axle such that a gap is defined between the first axle and the second axle,
wherein the end effector is operable to move the needle throwing arm and the needle receiving arm in an asynchronous fashion to repeatedly pass a surgical needle from the needle throwing arm to the needle receiving arm and back to the needle throwing arm along a circular path, wherein the circular path defines a plane that is substantially parallel to the longitudinal axis of the shaft such that the end effector is operable to move the surgical needle through at least one full revolution along the circular path.

2. The apparatus of claim 1, wherein the end effector includes a pivot, wherein the pivot is fixed relative to the shaft, wherein the needle throwing arm is pivotable about the pivot, wherein the needle receiving arm is also pivotable about the pivot.

3. The apparatus of claim 1, wherein the first axle is aligned with the second axle.

4. An apparatus, comprising:
(a) a shaft, wherein the shaft defines a longitudinal axis; and
(b) an end effector, wherein the end effector comprises:
(i) a needle throwing arm, wherein the needle throwing arm is operable to selectively engage a surgical needle,
(ii) a first axle, wherein the needle throwing arm is pivotable about the first axle along a plane that is substantially parallel to the longitudinal axis of the shaft,
(iii) a needle receiving arm, wherein the needle receiving arm is operable to selectively engage a surgical needle transferred from the needle throwing arm, and
(iv) a second axle, wherein the needle receiving arm is pivotable about the second axle along a plane that is substantially parallel to the longitudinal axis of the shaft,
wherein the first axle is aligned with the second axle,
wherein the end effector is operable to repeatedly pass a surgical needle from the needle throwing arm to the needle receiving arm and back to the needle throwing arm by rotating the needle throwing arm in full revolutions and by rotating the needle receiving arm in full revolutions.

5. The apparatus of claim 4, wherein the end effector is operable to repeatedly pass a surgical needle from the needle throwing arm to the needle receiving arm and back to the needle throwing arm by moving the needle along a circular path in a single angular direction.

6. An apparatus, comprising:
(a) a shaft, wherein the shaft defines a longitudinal axis;
(b) an end effector, wherein the end effector comprises:
(i) a needle throwing arm, wherein the needle throwing arm includes a needle grasping feature operable to selectively engage a surgical needle,
(ii) a first axle, wherein the needle throwing arm is pivotable about the first axle along a plane that is substantially parallel to the longitudinal axis of the shaft;
(iii) a needle receiving arm, wherein the needle receiving arm includes a needle grasping feature operable to selectively engage a surgical needle transferred from the needle grasping feature of the needle throwing arm, and
(iv) a second axle, wherein the needle receiving arm is pivotable about the second axle along a plane that is substantially parallel to the longitudinal axis of the shaft, wherein the first axle is aligned with the second axle;
(c) a first actuator, wherein the first actuator is operable to move the needle grasping feature of the needle throwing arm along a substantially circular path only in a single direction upon reciprocation of the first actuator relative to the shaft; and
(d) a second actuator, wherein the second actuator is operable to move the needle grasping feature of the needle receiving arm along a substantially circular path only in a single direction upon reciprocation of the second actuator relative to the shaft;
wherein the end effector is operable to repeatedly pass a surgical needle from the needle throwing arm to the needle receiving arm and back to the needle throwing arm by rotating the needle throwing arm in full revolutions and by rotating the needle receiving arm in full revolutions.

* * * * *